United States Patent
Hammons et al.

[19]

[11] Patent Number: 5,873,869
[45] Date of Patent: Feb. 23, 1999

[54] ABSORBENT ARTICLE WITH FOAM ABSORBENT STRUCTURE PROVIDING IMPROVED MENSES ACQUISITION AND FIT

[75] Inventors: John Lee Hammons, Hamilton; John Collins Dyer, Cincinnati, both of Ohio

[73] Assignee: The Procter & Gamble Company, Cincinnati, Ohio

[21] Appl. No.: 675,138

[22] Filed: Jul. 3, 1996

Related U.S. Application Data

[63] Continuation-in-part of Ser. No. 397,592, Mar. 2, 1995, abandoned, and a continuation-in-part of Ser. No. 542,497, Oct. 13, 1995, Pat. No. 5,849,805.

[51] Int. Cl.[6] .............................. A61F 13/15; A61F 13/20
[52] U.S. Cl. .................. 604/385.1; 604/369; 604/387
[58] Field of Search ................... 604/378, 385.1, 604/368, 369, 367, 374, 379, 380, 387

[56] References Cited

U.S. PATENT DOCUMENTS

| | | |
|---|---|---|
| H1614 | 11/1996 | Mayer et al. . |
| H1634 | 2/1997 | Oetjen et al. . |
| 2,747,575 | 5/1956 | Mercer . |
| 3,903,232 | 9/1975 | Wood et al. . |
| 4,049,592 | 9/1977 | Marans et al. . |
| 4,110,276 | 8/1978 | DesMarais . |
| 4,425,130 | 1/1984 | DesMarais . |
| 4,613,543 | 9/1986 | Dabi . |
| 4,752,349 | 6/1988 | Gebel . |
| 4,940,462 | 7/1990 | Salerno .................................... 604/387 |
| 4,950,264 | 8/1990 | Osborn, III . |
| 5,009,653 | 4/1991 | Osborn, III . |
| 5,147,345 | 9/1992 | Young et al. . |
| 5,260,345 | 11/1993 | DesMarais et al. . |
| 5,268,224 | 12/1993 | DesMarais et al. . |
| 5,318,554 | 6/1994 | Young et al. . |
| 5,331,015 | 7/1994 | DesMarais . |
| 5,336,208 | 8/1994 | Rosenbluth et al. .................... 604/387 |
| 5,387,207 | 2/1995 | Dyer et al. . |
| 5,454,801 | 10/1995 | Lauritzen ................................ 604/387 |
| 5,571,849 | 11/1996 | DesMarais . |
| 5,599,334 | 2/1997 | Johnston et al. ....................... 604/387 |

FOREIGN PATENT DOCUMENTS

| | | |
|---|---|---|
| 0 685 212 A2 | 4/1995 | European Pat. Off. . |
| WO 94/16658 | 8/1994 | WIPO . |
| WO 96/00550 | 6/1995 | WIPO . |
| WO 96/05790 | 7/1995 | WIPO . |
| WO 96/16624 | 11/1995 | WIPO . |
| WO 96/26699 | 2/1996 | WIPO . |

*Primary Examiner*—John G. Weiss
*Assistant Examiner*—Ki Yong O
*Attorney, Agent, or Firm*—Jeffrey V. Bamber; Steven W. Miller; Jacobus C. Rasser

[57] ABSTRACT

Absorbent articles such as sanitary napkins, panty liners, adult incontinence devices, and the like are disclosed. The absorbent articles described herein comprise a foam absorbent structure comprising a hydrophilic, flexible, nonionic polymeric foam structure of interconnected open cells which is particularly suitable for absorbing blood and blood-based liquids. The foam structure is resiliently compressible and has resistance to compression deflection of from about 5% to about 85% when measured under a confining pressure of 0.74 psi at 31° C. after 15 minutes. In preferred embodiments, the foam structure is compressible under such forces that when it is placed in the space between the wearer's labia majora, it will be compressed without deforming the wearer's labia majora, and will be molded by the wearer's labia and conform to the shape thereof. The absorbent structure may comprise an acquisition/fit portion and a storage portion wherein the acquisition/fit portion has softer mechanical properties than the storage portion, and is a capillary gradient in the direction of the storage portion.

22 Claims, 7 Drawing Sheets

ABSORBENT ARTICLE WITH FOAM ABSORBENT STRUCTURE PROVIDING IMPROVED MENSES ACQUISITION AND FIT

CROSS-REFERENCE TO RELATED APPLICATIONS

This is a continuation-in-part of the following U.S. patent applications: Ser. No. 08/397,592 filed Mar. 2, 1995; and Ser. No. 08/542,497 filed Oct. 13, 1995 now U.S. Pat. No. 5,849,805.

FIELD OF THE INVENTION

The present invention relates to absorbent articles such as sanitary napkins, panty liners, and the like. More particularly, the present invention relates to absorbent articles of the foregoing type which have a foam absorbent structure that provide improved acquisition of blood based liquids such as menses, and improved fit relative to a female wearer's body.

BACKGROUND OF THE INVENTION

Absorbent articles such as sanitary napkins, pantiliners, and incontinence pads are devices that are typically worn in the crotch region of an undergarment. These devices are designed to absorb and retain liquid and other discharges from the human body and to prevent body and clothing soiling. Sanitary napkins are a type of absorbent article worn by women in a pair of panties that is normally positioned between the wearer's legs, adjacent to the perineum. Sanitary napkins of a wide variety of shapes and dimensions are currently used by women for the collection of menses and other bodily discharges.

In the past, a number of efforts have been directed at providing sanitary napkins that maintain contact with the wearer's body. One attempt to provide such body contact is disclosed in U.S. Pat. No. 2,747,575 issued May 29, 1956 to Mercer. The Mercer patent discloses a catamenial bandage having a longitudinal hump which bulges towards and may contact the body of the wearer, The catamenial bandage described in the Mercer patent suffers from several disadvantages, however. For instance, the size and shape of the absorbent pad and hump in the Mercer bandage appear to limit the conditions under which the bandage is able to maintain contact with (and conform to) the body of the wearer. The portions of the bandage that lie laterally to the sides of the hump are not thin and flexible. In addition, the hump of the Mercer bandage is made of a cellulosic material, and, as a result, may tend to collapse and become permanently distorted during use.

U.S. Pat. No. 4,425,130 issued to DesMarais on Jan. 10, 1984, discloses a compound sanitary napkin that comprises a primary menstrual pad and a panty protector joined to one another at their corresponding ends in such a manner that the two constituents are free to move relative to one another along essentially their entire common length. The primary menstrual pad is intended to absorb the bulk of the bodily fluids discharged by the user, while the panty protector is intended to protect the user's garments from soiling. In use, the relative freedom of movement between the primary menstrual pad and the panty protector serves to maintain the primary menstrual pad adjacent the user's crotch region while the panty protector remains associated with the user's undergarment.

The current tendency has been to develop sanitary napkins that are increasingly thinner, and thus more comfortable and less obtrusive than prior sanitary napkins. Recently, efforts have been directed at developing thin sanitary napkins which have the capacity to absorb and contain medium to high menstrual discharges. Previously, such discharges could only be handled by relatively thick sanitary napkins. Examples of thin sanitary napkins having capacities great enough to handle medium to high menstrual flows are disclosed in U.S. Pat. Nos. 4,950,264 and 5,009,653, issued to Osborn, III, on Aug. 21, 1990 and Apr. 23, 1991, respectively.

It is also desirable that sanitary napkins, not only maintain contact with, but conform as closely as possible to the wearer's body. Such a body-conforming capability increases the effectiveness of the sanitary napkin by reducing the possibility that menses will travel around the perimeter of the sanitary napkin and leak. There have been a number of recent efforts to provide sanitary napkins and other absorbent articles with improved body-conforming characteristics. In addition to serving as examples of thin sanitary napkins, the sanitary napkins disclosed in the above-mentioned Osborn patents also serve as examples of anatomically-conforming sanitary napkins. While the sanitary napkins disclosed in the Osborn patents work quite well, the search for improved sanitary napkins has continued.

For example, PCT International Patent Application Publication No. WO 94/16658, entitled "Generally Thin, Flexible Sanitary Napkin With Central Absorbent Hump", published on Aug. 4, 1994, discloses a generally thin, flexible sanitary napkin which has a central absorbent hump, and is capable of handling medium to high menstrual flows. The hump is particularly useful in fitting into the space between the wearer's labia to more readily intercept menses and other bodily discharges when they leave the wearer's body. The search, however, has continued for improved sanitary napkins, particularly sanitary napkins that will achieve even better fit within the space between the wearer's labia majora, and which are more adept at absorbing blood-based liquids, such as menses.

The development of highly absorbent articles for blood and blood-based liquids such as catamenial pads (e.g., sanitary napkins), tampons, wound dressings, bandages and surgical drapes can be challenging. Compared to water and urine, blood and blood based liquids such as menses are relatively complex mixtures of dissolved and undissolved components (e.g., erythrocytes or red blood cells). In particular, blood-based liquids such as menses are much more viscous than water and urine. This higher viscosity hampers the ability of conventional absorbent materials to efficiently and rapidly transport these blood-based liquids to regions remote from the point of initial discharge. Undissolved elements in these blood-based liquids can also potentially clog the capillaries of these absorbent materials. This makes the design of appropriate absorbent systems for blood-based liquids such as menses particularly difficult.

Foams of various types have been suggested for use in tampons, sanitary napkins and other articles that absorb blood and blood-based liquids. See for example U.S. Pat. No. 4,110,276 (DesMarais), issued Aug. 29, 1978 (soft, flexible, open celled foams made from polyurethanes, cellulose, or styrene/butadiene rubber that can be used in tampons and sanitary pads); U.S. Pat. No. 4,752,349 (Gebel), issued Jun. 21, 1988 (foams of "medium cell size" hydrophilized by surfactant treatment and having a density within the range of 0.1 to 0.8 g/cc); U.S. Pat. No. 4,613,543 (Dabi), issued Sep. 28, 1986 (hydrophilic cellular polymers used in catamenial products); U.S. Pat. No. 3,903,232 (Wood et al.), issued Sep. 2, 1975 (compressed hydrophilic polyurethane foams useful in biomedical applications, including catamenial devices); U.S. Pat. No. 4,049,592 (Marans et al.) issued Sep. 20, 1977 (biodegradable hydrophilic polyurethane foams highly absorptive upon contact with liquids or bodily liquids having utility in sanitary napkins and the like). Prior foams used in these products have tended to have relatively large cell sizes. As a result, these prior foams do not exert sufficient fluid capillary pressure for blood and blood-based liquids to acquire discharged menstrual liquids quickly from and through the topsheet of catamenial products such as sanitary napkin . This results in undesirable rewet since the surface in immediate contact with the body retains some of the fluid that is not absorbed into the core and is available to be transferred back onto the body of the wearer.

Suitable absorbent foams for absorbent products have also been made from High Internal Phase Emulsions (hereafter referred to as "HIPE"). See, for example, U.S. Pat. No. 5,260,345 (DesMarais et al), issued Nov. 9, 1993 and U.S. Pat. No. 5,268,224 (DesMarais et al), issued Dec. 7, 1993. These absorbent HIPE foams provide desirable urine handling properties, including: (a) relatively good wicking and fluid distribution characteristics to transport fluid away from the initial impingement zone and into the unused balance of the foam structure to allow for subsequent gushes of fluid to be accommodated; and (b) a relatively high storage capacity with a relatively high fluid capacity under load, i.e. under compressive forces. These HIPE absorbent foams are also sufficiently flexible and soft so as to provide a high degree of comfort to the wearer of the absorbent article; some of these foams, such as those described in U.S. Pat. No. 5,387,207 issued Feb. 7, 1995 (Dyer, et al.), can be made relatively thin until subsequently wetted by the absorbed body liquids. See also U.S. Pat. No. 5,147,345 (Young et al), issued Sep. 15, 1992 and U.S. Pat. No. 5,318,554 (Young et al), issued Jun. 7, 1994, which disclose absorbent cores having a fluid acquisition/distribution component that can be a hydrophilic, flexible, open-celled foam such as a melamine-formaldehyde foam (e.g., BASOTECT™ made by BASF), and a fluid storage/redistribution component that is a HIPE-based absorbent foam.

HIPE foams can provide the fluid capillary pressure necessary to remove most of the menstrual fluid from the body, or topsheet adjacent to the body, thus minimizing rewet. However, it has been found that the residual hydratable salts such as calcium chloride typically present in prior HIPE foams can impair the rapid acquisition blood and blood-based liquids by these foams, and especially the wicking of such liquids within these foams. As noted above, blood and blood-based liquids such as menses are more highly viscous than water and especially urine. The higher viscosity of these liquids is further increased by the presence of these salts. Moreover, prior HIPE foams often had a foam microstructure too small to admit readily the undissolved components of blood and blood-based liquids such as red blood cells.

Therefore, it is an object of the present invention to provide an absorbent article, such as a sanitary napkin that maintains contact with and conforms as closely as possible to the wearer's body.

It is another object of the present invention to provide an absorbent article, such as a sanitary napkin that is comprised of a foam material which is especially suitable for handling, absorbing, and storing blood-based liquids, such as menses.

It is another object of the present invention to provide an absorbent structure for an absorbent article, where the entire absorbent structure is absorbent and resilient so that the absorbent article does not require a separate resilient component that would interfere with the overall absorbency of the absorbent structure.

It is another object of this invention to provide a sanitary napkin which readily intercepts menses when discharged by being highly compressible so that it can be compressed to a relatively small size to comfortably fit and maintain contact with and conform to the shape of the female wearer's body, particularly with the inwardly-facing surfaces of the labia majora, or it can occupy the relatively large area in the crevice between the wearer's buttocks (or gluteal groove).

It is an additional object of the present invention to provide an absorbent article, such as a sanitary napkin, that has an absorbent structure which can routinely and comfortably fit interlabially on wearer's having a wide variety of body dimensions.

These and other objects of the present invention will be more readily apparent when considered in reference to the following description and when taken in conjunction with the accompanying drawings.

SUMMARY OF THE INVENTION

The present invention is directed to absorbent articles for wearing by a human female such as sanitary napkins, panty liners, interlabial devices, and adult incontinence pads which provide improved acquisition of blood-based liquids such as menses, and improved fit relative to a female wearer's body.

The absorbent article comprises a primary absorbent component having a base and an apex. In one preferred embodiment, the width of the base is greater than the width of the apex and the width of said primary absorbent component decreases from the base to the apex. Preferably, at least a portion of the primary absorbent component has a width of less than or equal to about 9.5 mm, or is compressible to such a width. The primary absorbent component comprises a compressible and resilient, hydrophilic, flexible, nonionic polymeric foam structure of interconnected open cells which is capable of absorbing blood and blood-based liquids. The foam structure is compressible under such forces that when it is placed in the space between the wearer's labia majora, it will be compressed without deforming the wearer's labia, and will be molded by the wearer's labia and conform to the shape thereof The absorbent article is, thus, very comfortable to wear. In addition, in a particularly preferred embodiment, the absorbent article is provided in the form of a sanitary napkin in which the primary absorbent component will be able to fit in the space between the wearer's labia (and gluteal groove) by the simple action of placing the sanitary napkin in a pair of panties, and pulling up the panties.

The foam materials used in the absorbent article of the present invention are capable of absorbing blood and blood-based liquids such as menses and then moving these absorbed liquids efficiently to other regions of the foam. These absorbent polymeric foam materials comprise a hydrophilic, flexible, nonionic polymeric foam structure of interconnected open-cells. This foam structure has:

A) the ability to wick artificial menstrual fluid (AMF) vertically to a height of 5 cm in less than about 40 minutes;

B) a capillary specific surface area in the range of from about 0.0080 to about 0.040 $m^2$/cc;

C) a resistance to compression deflection of from about 5 to about 85% when measured under a confining pressure of 0.74 psi at 31° C. after 15 minutes;

D) a free absorbent capacity of from about 20 to about 125 g/g;

E) less than about 2% of residual hydratable salts.

A particularly important attribute of the foams used in the present invention is that the connecting passages (holes) between the cells of these foams are sufficiently large to pass insoluble solids such as erythrocytes (mean diameter 8 μm). As a result, these holes do not become blocked or obstructed by blood and blood-based liquids absorbed by the foam. Even though the cells and holes are large enough to allow free movement of insoluble components in blood and blood-based liquids, they are sufficiently small so as to produce the necessary high capillary absorption pressure required of absorbents used in catamenial products. In other words, these foams combine high capillary absorption pressure with sufficient openness to allow free movement of the insoluble components in blood and blood-based liquids such as menses. Typically, the cells of these foams have a number average cell size of from about 30 to about 130 μm, while the holes between these cells have a number average hole size of from about 5 μm to about 30 μm.

The process of forming the foams used in the present invention allows these absorbent foams to have cells and holes small enough to provide a high capillary absorptive pressure but large enough to prevent or minimize blockage by the insoluble components of these liquids. In addition, this process removes most of the residual electrolytes (i.e., hydratable salts) from the foam. While these hydratable salts are typically needed during initial formation of the HIPE, their presence in the resulting foam can adversely affect its ability to absorb blood and blood-based liquids such as menses, especially as the concentration of these salts in the foam increases. Accordingly, it is desirable to reduce the level of these hydratable salts in the foam.

In one preferred embodiment, the absorbent article comprises a primary absorbent component, comprising an acquisition/fit portion and a storage portion. The acquisition/fit portion comprises a hydrophilic, flexible, nonionic polymeric foam structure of interconnected open cells which is capable of absorbing blood and bloodbased liquids. The foam structure forming the acquisition/fit portion has a first width and the cells within the foam structure are of a size within a first range of values (or first average cell diameter or "cell size"). The storage portion also comprises a hydrophilic, flexible, nonionic polymeric foam structure of interconnected open cells which is capable of absorbing blood and blood-based liquids. The foam structure forming the storage portion has a second width and the cells within the foam structure have a second cell size (or second average cell diameter or "cell size"), wherein the second cell size is smaller than the first cell size and the first width is less than the second width.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

DETAILED DESCRIPTION OF THE INVENTION

1. General Characteristics of a Preferred Embodiment of the Absorbent Article of the Present Invention.

The present invention is directed to absorbent articles for wearing by a human female such as sanitary napkins, panty liners, interlabial devices, and adult incontinence pads. The absorbent articles of the present invention have a foam absorbent structure that provides improved acquisition of blood-based liquids such as menses, and improved fit relative to a female wearer's body.

Figure 1:
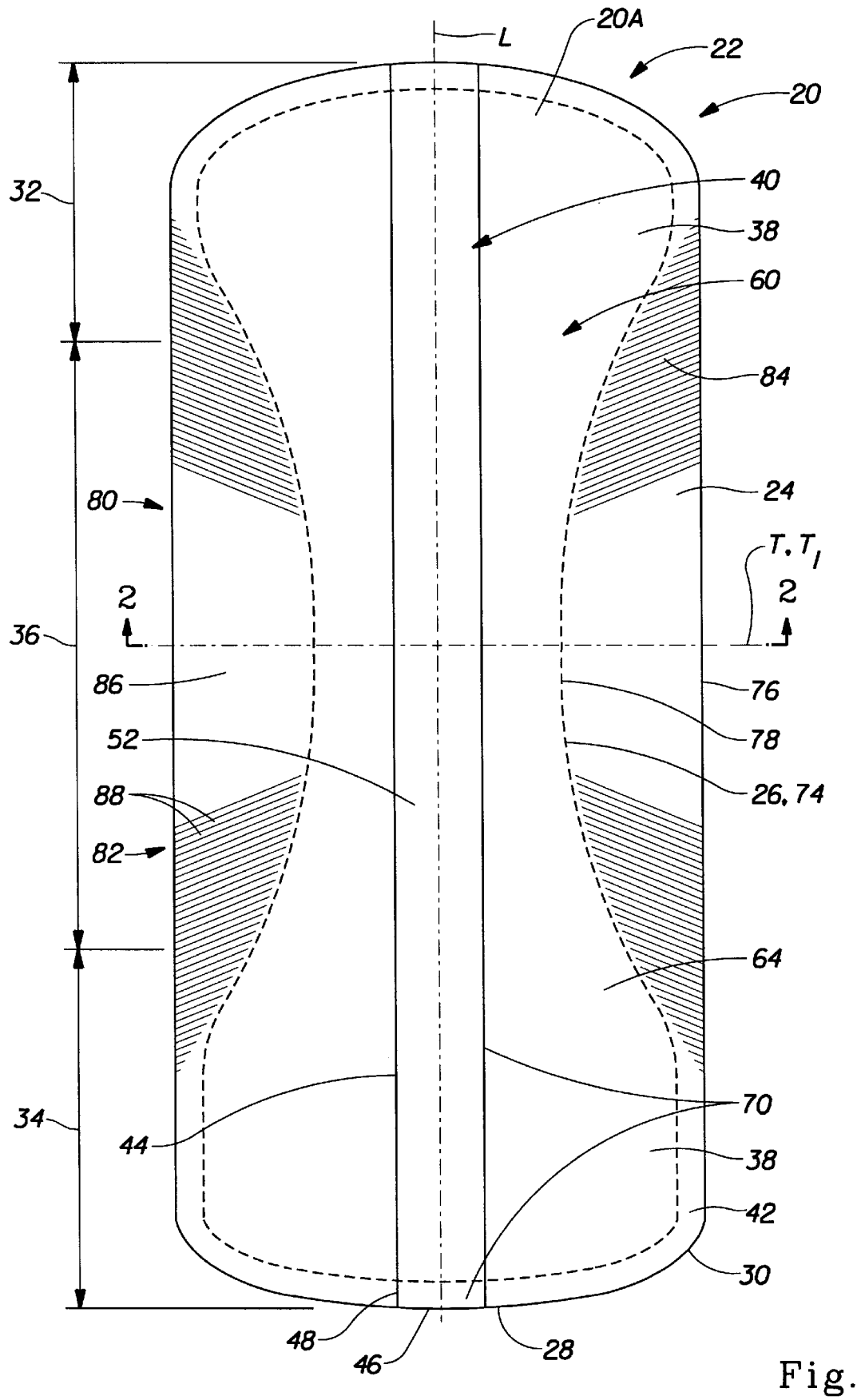
FIG. 1 is a top plan view of a preferred embodiment of a sanitary napkin of the present invention.
Figure 2:
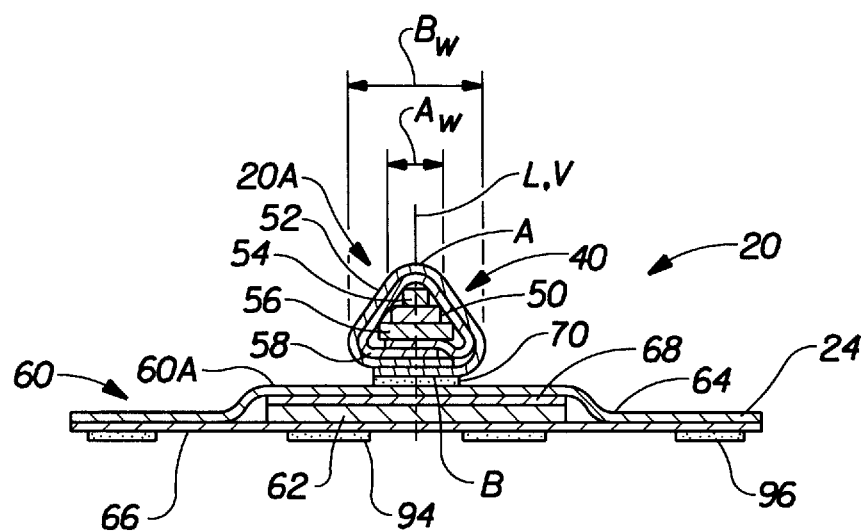
FIG. 2 is a cross-sectional view of the sanitary napkin shown in FIG. 1, taken along line 2—2.
Figure 3:
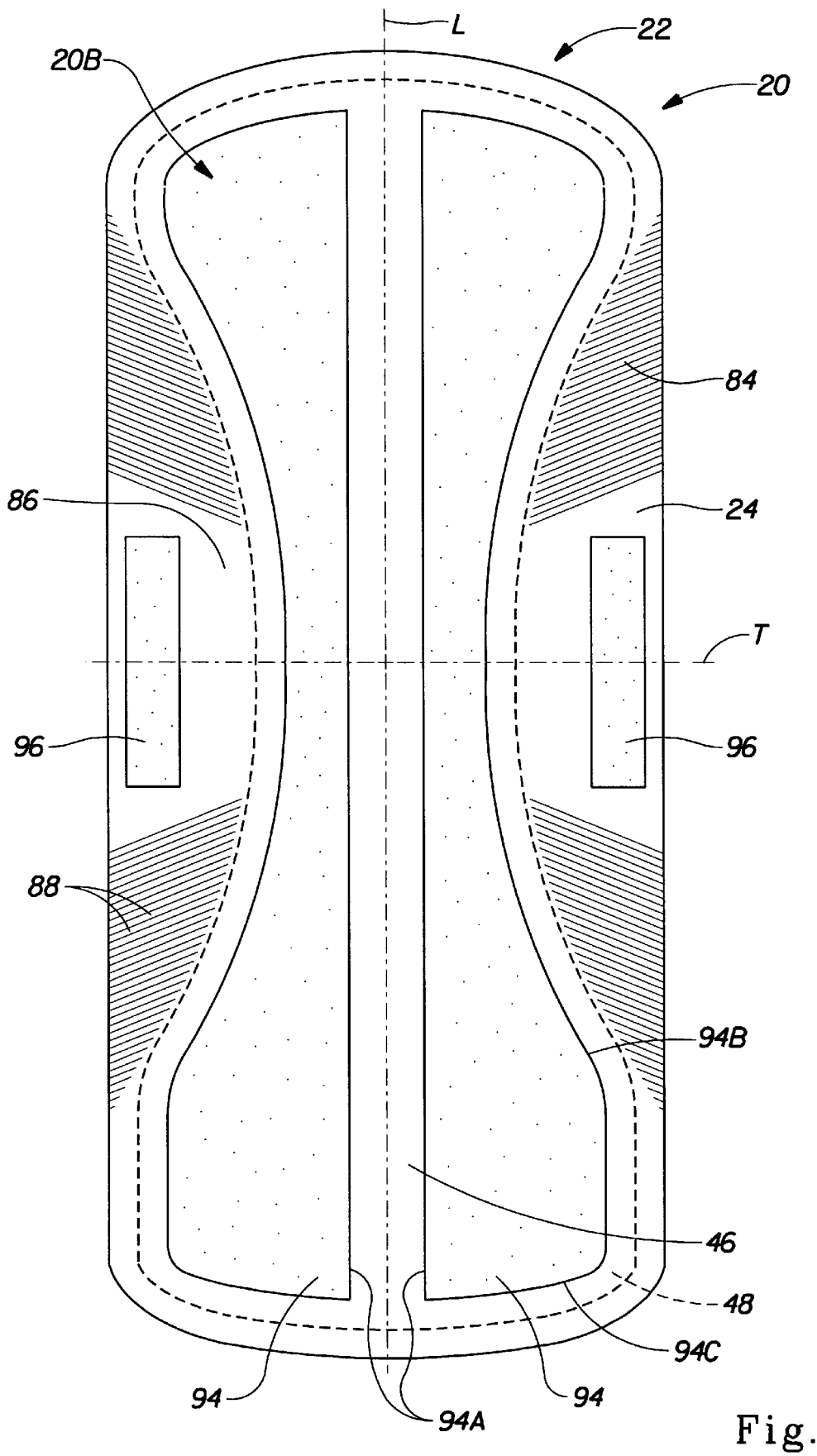
FIG. 3 is a bottom plan view of the sanitary napkin shown in FIG. 1.

The absorbent article comprises a primary absorbent component having a base and an apex. In one preferred embodiment, the width of the base is greater than the width of the apex and the width of said primary absorbent component decreases from the base to the apex. The primary absorbent component comprises a compressible, hydrophilic, flexible, nonionic polymeric foam structure of interconnected open cells which is capable of absorbing blood and blood-based liquids. The foam structure is compressible under such forces that when it is placed in the space between the wearer's labia majora, it will be compressed without deforming the wearer's labia, and will be molded by the wearer's labia and conform to the shape thereof FIGS. 1–3 show one preferred embodiment of a sanitary napkin 20 of the present invention, in the form of a compound sanitary napkin that is preferred for night time use. As shown in FIG. 1, the sanitary napkin 20 basically comprises a main body portion 22 and two side extensions or side wrapping elements 24. The main body portion 22 of the sanitary napkin 20 comprises a primary absorbent member (or "primary absorbent component" or "core tube") 40 and a secondary absorbent member (or "secondary absorbent component" or "base pad") 60 that are joined together by union means 70. The compound sanitary napkin 20 has two surfaces, a body-contacting or body-facing surface 20A, and a garment-facing or garment-contacting surface 20B. The primary absorbent member 40 and secondary absorbent member 60 also each have corresponding body-facing and garment-facing surfaces.

The compound sanitary napkin 20 has two centerlines, a longitudinal centerline L and a transverse centerline T. The term "longitudinal", as use herein, refers to a line, axis or direction in the plane of the compound sanitary napkin that is generally aligned with (e.g., approximately parallel to) a vertical plane which bisects a standing wearer into left and right body halves when the compound sanitary napkin is worn. The terms "transverse" or "ateral", as used herein, are interchangeable, and refer, to a line, axis, or direction which lies within the plane of the sanitary napkin that is generally perpendicular to the longitudinal direction.

FIG. 1 shows that the main body portion 22 of the sanitary napkin 20 comprises the portion of the sanitary napkin without the side wrapping elements 24. The main body portion 22 has two spaced apart longitudinal edges 26, two spaced apart transverse or end edges (or "ends") 28, which together form the periphery 30 of the main body portion 22 of the sanitary napkin 20. The main body portion 22 also has two end regions, which are designated first end region 32 and second end region 34. A central region 36 is disposed between the end regions 32 and 34. The end regions 32 and 34 extend outwardly from the edges of the central region 36 about 1/8 to about 1/3 of the length of the main body portion. A detailed description of the central region and two end regions for a sanitary napkin is contained in U.S. U.S. Pat. No. 4,690,680 issued to Higgins on Sep. 1, 1987.

The main body portion 22 of the sanitary napkin 20 is preferably hourglass shaped or dog bone shaped. The first and second end regions 32 and 34, of the main body portion 22 preferably comprise lobes 38 that extend laterally outward at each longitudinal edge 26 of the main body portion so that the main body portion 22 is narrower in width when measured across the central region 36 than at its end regions 32 and 34. The outermost edges of the lobes 38, thus define portions of the longitudinal side edges 26 of the main body portion 22, A portion of the longitudinal side edges 26 in the region of the lobes 38 will typically define the laterally outwardmost portion 42 of the main body portion 22.

The sanitary napkin 20 shown in FIG. 1 can be of any suitable size. Preferably, the embodiment of the sanitary napkin 20 shown in the drawings is of a size sufficient to allow the side wrapping elements 24 to fold along a curvilinear line along the elasticized side edges of a wearer's panties as described in greater detail hereinafter. In this embodiment, the sanitary napkin 20, and the main body portion 22 thereof, are preferably also relatively large in size so that they are able to cover the maximum area of the wearer's panties to reduce or eliminate soiling of the same by the wearer's bodily fluids, particularly for night time usage. In one preferred embodiment, the main body portion 22 of the sanitary napkin 20 is about 3.25 inches (8.26 cm) wide at its narrowest point. The overall sanitary napkin 20 in such an embodiment is approximately 14.75 inches (37.5 cm) in length measured along the longitudinal centerline L, and about 6.25 inches (about 16 cm) in width (measured between the distal edges of the side wrapping elements). In another embodiment, the width of the sanitary napkin 20 is the same, but the length ranges from about 31.7 cm to about 34.5 cm. In other, more conventionally-sized embodiments, such as those intended for day time use, the main body portion 22 is preferably from about 20 to 40 cm long, more preferably from about 22 to 35 cm long, and most preferably is about 24 cm long. The main body portion 22 is preferably from about 5 to 15 cm in width, more preferably from about 5 to 10 cm in width, and most preferably from about 5 to 8 cm in width.

The main body portion 22 of the sanitary napkin 20 can be of any thickness, including relatively thick, intermediate (or moderate) thickness, relatively thin, or even very thin. The embodiment of the sanitary napkin 20 shown in FIGS. 1–3 of the drawings comprises a relatively thick, but compressible and conformable, primary absorbent member 40 disposed on top of a relatively thin secondary absorbent member 60. It should be understood that the sanitary napkin shown is merely one preferred embodiment, and that the present invention is not limited to absorbent articles of the type or having the specific configurations shown in the drawings.

2. Individual Components of the Absorbent Article

FIG. 2 shows the individual components of the main body portion 22 of the sanitary napkin 20 of the present invention. The main body portion 22 of the compound sanitary napkin shown in the drawings, as discussed above, basically comprises a primary absorbent member 40 and a secondary absorbent member 60.

A. The Primary Absorbent Member.

1. General Characteristics.

The primary absorbent member 40 is the portion of the compound sanitary napkin 20 that is intended to absorb the bulk of bodily fluids discharged by the user. The primary absorbent member 40 has side edges 44 and end edges 46 which together form the periphery 48 of the primary absorbent member 40. The primary absorbent member 40 comprises an absorbent structure, such as absorbent core (or foam absorbent core) 50, and an outer cover 52 superimposed on the foam absorbent core 50. (As used herein, the term "superimposed" means adjacent or juxtaposed, but not necessarily in contact with or joined to.) As shown in FIG. 2, the primary absorbent member 40 has a vertical centerline V, a base B having a width $B_w$, and an apex A vertically opposed to the base B, having a width $A_w$. As used herein, the term "base" refers to that portion of the primary absorbent member 40 which is juxtaposed with the body-facing surface 60A of the secondary absorbent member 60.

It has been found that the general shape of the primary absorbent member 40 can affect the absorbent characteristics of the sanitary napkin 20 as well as the overall comfort to the wearer. Generally, a compound sanitary napkin comprising a primary absorbent member 40 having a base, B, that is wider than the apex (that portion of the primary absorbent member 40 intended to fit at least partially within the external female genitalia), A, will have increased effectiveness and comfort. (The "width" at any given location is determined by measuring the lateral or transverse dimension at that location. Thus, width measurements are taken generally parallel to the transverse centerline T.)

The primary absorbent member 40 is not limited to any particular shape or width, so long as the base B has a width $B_w$ which is greater than the apex A width $A_w$. As shown in FIG. 2 in preferred embodiments of the present invention, the primary absorbent member 40 has a generally triangular cross-section when it is not subjected to any stresses. The shape of the primary absorbent member 40 is defined by an absorbent core 50 comprising a plurality of stacked strips of decreasing width from the base B to the apex A. In other embodiments, however, the absorbent core 50 may comprise a wide variety of shapes such as rectangular, oval, trapezoidal, pentagonal, U-shaped, Z-folded, and still provide the primary absorbent member 40 with a base width $B_w$ greater than apex width $A_w$.

The primary absorbent member 40 is preferably roughly centered along the longitudinal and transverse centerlines L and T. At least a portion of the base B is preferably joined with, or in face-to-face contact with the body facing surface 60A of the secondary absorbent member 60. (As used herein, the term "joined" encompasses configurations whereby an element is directly secured to another element by affixing the element to the other element; configurations whereby an element is indirectly secured to another element by affixing the element to an intermediate member or members which in turn are affixed to the other element; and configurations in which one element is integral with another element, i.e., one element is essentially part of the other element.)

The apex A may be of any shape and may have any width Aw that is less than the width $B_w$ of the base B. Preferably, the apex A is shaped and sized to comfortably reside at least partially within the external female genitalia. Thus, as shown in cross-section in FIG. 2, the apex A is preferably at least partially curved or rounded for improved comfort, or otherwise shaped to conform to the wearer's body. Other embodiments, however, are contemplated wherein the apex A is flat, pointed, or generally non-curvilinear.

The primary absorbent member 40 can be of any suitable size. In the preferred embodiment shown, the primary absorbent member 40 and the secondary absorbent member 60 are of the same length. However, it is quite possible for the primary absorbent member 40 to be shorter than the secondary absorbent member 60 and still function effectively. Thus, the length of the primary absorbent member 40 can range up to the lengths described herein for the secondary absorbent member 60. In conventionally-sized embodiments, such as those intended for day time use, the primary absorbent member 40 is preferably from about 2 to 35 cm long, more preferably from about 10 to 35 cm long, and most preferably from about 20 to 35 cm long. A particularly preferred primary absorbent member 40 for use in such a day time embodiment has a length of about 17 to 20 cm. The primary absorbent member 40 is preferably from about 0.5 to 5 cm wide at its base B, more preferably from about 0.5 to about 4 cm wide, and most preferably from about 0.5 to about 3 cm wide.

The dimensions of the primary absorbent member 40 can be related to each other in a variety of different ways. Preferably, however, the primary absorbent member 40 has a length that is relatively great in comparison to its height. This can be described in terms of the reciprocal of the height of the primary absorbent member 40 to its length. Preferably, the reciprocal of the height to length of the primary absorbent member 40 is between about 10 and about 50.

2. The Outer Cover.

The outer cover 52 comprises a component, at least a portion of which is liquid pervious to permit liquids to readily penetrate through its thickness. When the sanitary napkin 20 is in use, the outer cover 52 is in close proximity to the skin of the user. The outer cover 52 is preferably as compliant, soft feeling, and non-irritating to the user's skin as possible. The outer cover 52 should further exhibit good strikethrough and a reduced tendency to rewet, permitting bodily discharges to rapidly penetrate it and flow toward the core 50, but not allowing such discharges to flow back through the outer cover 52 to the skin of the wearer.

A suitable outer cover 52 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers); or from a combination of natural and synthetic fibers. The outer cover 52 may be a unitary member or it may be comprised of two or more elements joined together to form the outer cover 52. Further, any portion of the materials comprising the outer cover 52 may be coated, laminated, treated or otherwise manipulated to impart or enhance any desired characteristics such as strength, flexibility, liquid perviousness, or if desired, imperviousness.

A preferred outer cover 52 comprises an apertured formed film. Apertured formed films are preferred for the outer cover 52 because they are generally pervious to body exudates and if properly apertured, will reduce the likelihood of liquids passing back through the film and rewetting the wearer's skin. Accordingly, the surface of the formed film which is in contact with the body remains dry, thereby reducing body soiling and creating a more comfortable feel for the wearer. Further, if desired, formed films can be easily manufactured with non-apertured portions or regions that provide liquid impervious areas that prevent any liquids from passing therethrough. Suitable formed films are described in U.S. Pat. No. 3,929,135, issued to Thompson on Dec. 30, 1975; U.S. Pat. No. 4,324,246, issued to Mullane, et al. on Apr. 13, 1982; U.S. Pat. No. 4,342,314, issued to Radel, et al. on Aug. 3, 1982; U.S. Pat. No. 4,463,045, issued to Ahr, et al. on Jul. 31, 1984; and U.S. Pat. No. 5,006,394, issued to Baird on Apr. 9, 1991. One especially preferred outer cover 52 for the primary absorbent member 40 comprises a formed film described in one or more of the above patents and marketed on sanitary napkins by The Procter & Gamble Company of Cincinnati, Ohio as "DRI-WEAVE".

In a preferred embodiment of the present invention, the body-facing surface of at least a portion of the outer cover 52 is hydrophilic to help transfer exudate through the outer cover 52 more easily than if the body-facing surface was not hydrophilic. This diminishes the likelihood that body exudates will flow off the outer cover 52 rather than flowing into and being absorbed by the absorbent core 50. The body-facing surface of the outer cover 52 can be made hydrophilic by treating it with a surfactant. In a preferred embodiment, surfactant is incorporated into the polymeric materials of the formed film such as is described in such as described in U.S. Pat. No. 4,950,264 issued to Osborn on Aug. 21, 1990.

The primary absorbent member 40 may comprise a wrapper for the absorbent core 50, such as acquisition layer 58 shown in FIG. 2. The acquisition layer 58 may be a separate component positioned between the outer cover 52 and the absorbent core 50, or it may be an integral part of a composite outer cover. The acquisition layer 58 may serve several functions including improving wicking of exudates over and into the absorbent core 50. By improving the wicking of exudates, the acquisition layer 58 provides a more even distribution of the exudates throughout the absorbent core 50. The acquisition layer 58 may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of sanitary napkins having an acquisition layer are more fully described in U.S. Pat. No. 4,950,264 issued to Osborn and U.S. pat. application Ser. No. 07/944,764, "Absorbent Article Having Fused Layers", filed Oct. 7, 1992 in the names of Cree, et al. (PCT Publication No. WO 93/11725, published Jun. 23, 1993). In preferred embodiments, the acquisition layer 58 may be joined to the outer cover 52. These components can be joined by any of the conventional means for joining webs together, including, but not limited to joining the outer cover 52 to the acquisition layer 58 with adhesives such as by spray-gluing, by applying lines or spots of adhesives between the outer cover 52 and the acquisition layer 58, by wrapping the outer cover 52 about the acquisition layer 58, by fusing the outer cover 52 to the acquisition layer 58 with a plurality of discrete individual fusion bonds, or by any other means known in the art Referring now to FIG. 2, it can be seen that outer cover 52 completely wraps the absorbent core 50 of the primary absorbent member 40. In other embodiments, the outer cover 52 need not completely encircle the absorbent core 50.

In such embodiments, the outer cover 52 may substantially encircle the absorbent core 50. (As used herein, the term "substantially encircle" means that the outer cover overlays more than half of the absorbent core, and more preferably most of the absorbent core.) In the embodiments where the outer cover 52 does not completely encircle the absorbent core 50, a channel (or liquid passageway) may be formed between the primary absorbent member 40 and the secondary member 60. The channel can provide a passageway for any liquids not retained by the primary absorbent member 40 to pass through to the secondary absorbent member 60 so that they may be absorbed and contained therein.

3. The Foam Absorbent Core.

a. General Properties

The foam absorbent core (or absorbent foam component) 50 used in the sanitary napkin 20 of the present invention acquires, absorbs, and contains body exudates. The foam absorbent core 50 also maintains the shape of the primary absorbent member 40 so that the primary absorbent member 40 conforms to the shape of the wearer's body. Thus, the absorbent core 50 is preferably capable of absorbing and containing body exudates, and is compressible, conformable, resilient, and non-irritating to the wearer's skin.

The total absorbent capacity of the absorbent core 50 should be compatible with the intended exudate loading for the primary absorbent member 40. The primary absorbent component 40 preferably has a capacity equal to, and more preferably, greater than at least the lower end of the range of capacities of the sanitary napkins described in U.S. Pat. No. 4,950,264 and 5,009,653 issued to Osborn. The primary absorbent member 40 may, for example, have a total capacity of between about 20–60 grams of sterile saline measured according to the procedure set out in U.S. Pat. No. 5,009,653 issued to Osborn. Further, the absorbent capacity of the absorbent core 50 may be varied to accommodate wearers ranging in the expected amount of exudate fluid volume. For instance, a different absorbent capacity may be utilized for sanitary napkins intended for day time use as compared with those intended for night time use, or for sanitary napkins intended for use by teenage females as compared with those intended by more mature women.

The foam materials selected for use as the absorbent core 50 are preferably compliant, soft, comfortable, compressible, and resilient to enhance body fit and comfort of the primary absorbent member 40. Preferably, the absorbent core 50 is compressible so that the primary absorbent member 40 will deform under relatively small forces exerted by the external female genitalia that are experienced during normal use. In addition to being compressible, the foam materials comprising the absorbent core 50 are preferably conformable so that the primary absorbent member 40 is able to provide improved fit into and around the labia and perineum. It is also important that the primary absorbent member 40 be sufficiently resilient such that when subjected to normal wearing forces it does not permanently collapse. The absorbent core 50 provides the primary absorbent member 40 with the desired resilient characteristics so that the primary absorbent member 40 conforms to the contours of the body to provide intimate contact with the exposed genitalia of the female user. Intimate contact with the exposed female genitalia helps provide better transfer of liquid exudates from the user into the primary absorbent member 40 without allowing such liquids to bypass and/or run-off the primary absorbent member 40. While the resilient characteristics of the absorbent core 50 allow for improved fit, they must be balanced against the need for the product to be both soft and comfortable for the wearer.

The foam absorbent core 50 of the embodiment shown in the drawings comprises two main portions, an acquisition/fit portion 54 and a storage portion 56. The acquisition/fit portion 54 is the portion of the absorbent core 50 that is particularly suited for providing the absorbent core 50 with the ability to fit in close contact with and conform to the contours of the wearer's body, and to acquire and absorb bodily exudates from the wearer's body immediately upon discharge therefrom. The acquisition/fit portion 54 preferably also provides the absorbent core 50 with the desired resilient characteristics. The acquisition/fit portion 54 comprises a hydrophilic, flexible, nonionic polymeric foam structure of interconnected open cells which is capable of absorbing blood and blood-based liquids. The foam structure forming the acquisition/fit portion 54 has a first width and the cells within the foam structure are of a size within a first range of values (or first average cell diameter or "cell size").

The storage portion 56 is the portion of the absorbent core 50 that is particularly suited for obtaining bodily exudates, especially menses, from the acquisition/fit portion 54, and permanently storing such exudates. The storage portion 56 preferably also comprises a hydrophilic, flexible, nonionic polymeric foam structure of interconnected open cells which is capable of absorbing blood and bloodbased liquids. The foam structure forming the storage portion 56 has a second width and the cells within the foam structure have a second cell size (or second average cell diameter or "cell size").

Preferably, the acquisition/fit portion 54 and the storage portion 56 are provided with different properties. The acquisition/fit portion 54 and the storage portion 56 may differ in size, the type of foam used, the cell size of the foam, the resistance to compression of the foam, and absorbent capacity, to list a few possible differences. The different properties are preferred since the storage portion 56 should be able to take liquids from the fit/acquisition portion 54, to store those liquids, and need not be in as close contact with the wearer's body as the acquisition/fit portion 54. The acquisition/fit portion 54 preferably has softer mechanical properties which may be achieved by virtue of a lower Tg, higher W:O ratio, lower cross-linker levels, or a combination of such properties accompanied by a coarser cellular microstructure as compared with the storage portion 56.

Preferably, the acquisition/fit portion 54 is narrower in width than the storage portion 56. In especially preferred embodiments, the components of the absorbent core 50 are of a size and compressibility that at least a portion of the primary absorbent member 40 will fit comfortably within and fill the space between the wearer's labia majora without deforming the wearer's labia majora so that the primary absorbent member 40 will be molded by the wearer's labia majora and conform to the shape thereof in the front portion of the sanitary napkin 20, and substantially fill the gluteal groove (or crevice between the wearer's buttocks) in the rear. In order to do this, the absorbent core 50 can be provided with a fairly high amount of bulk. However, due to the compressibility and conformability of the foam material, even though it is bulky, it is very comfortable for the wearer.

The primary absorbent member 40 may, for example, have a volume of at least about 15 $cm^3$, preferably at least about 20 $cm^3$, and most preferably at least about 30 $cm^3$. The primary absorbent member 40 preferably has the specified volume(s) when in a compressed condition under the forces similar to those encountered during wear (and, of course, also in an uncompressed condition). The volume of the primary absorbent member can be measured during use, or under a simulated in-use load such as that applied during the RTCD test described herein. If the primary absorbent member 40 has the specified volume as measured in either manner, then it will be considered to have the volume(s) specified herein.

The overall primary absorbent member 40 for embodiments like that shown in the drawings, preferably ranges in height from about 5 mm to a maximum of between about 30 to 40 mm in its uncompressed state. In other embodiments, such as embodiments designed for use in Japan where the sanitary napkin is held closer to the wearer's body by menstrual shorts, the height does not need to even be this great to provide a certain amount of body contact. The overall primary absorbent member 40 for embodiments like that shown in the drawings preferably ranges in width from about 5 mm to about 50 to 60 mm. Preferably, the primary absorbent member 40 is about 25–30 mm wide at the base and tapers to less than about ⅜ inch (about 9.5 mm), and more preferably about ¼ inch (about 5 mm) at the apex, for that portion that will be placed in the area of the weaer's labia. It is also possible that the primary absorbent member could have dimensions slightly greater than these dimensions, and be compressible down to these dimensions in use.

The overall characteristics of the foam used for both the acquisition/fit portion 54 and the storage portion 56 will now be examined. The acquisition/fit portion 54 can comprise the same type of foam as the storage portion 56, or the acquisition/fit portion 54 and storage portion 56 can comprise different types of foam. Preferably, the acquisition/fit portion 54 and the storage portion 56 comprise the same basic type of foam composition. In addition, the acquisition/fit portion 54 and the storage portion 56 can either comprise different portions of a single unitary piece of foam (that is, they can form an integral absorbent core or absorbent component), or they can comprise separate components (or pieces) of foam. When the acquisition/fit portion 54 and the storage portion 56 comprise separate components, the acquisition/fit portion 54 and the storage portion 56 may be referred to as an acquisition/fit component 54 and a storage component 56, respectively.

The foams used in the absorbent structure of the present invention are open-celled polymeric foams. For purposes of the present invention, a foam material is "open-celled" if at least 80% of the cells in the foam structure that are at least 1 μm size are in liquid communication with at least one adjacent cell. The foams used in the foam absorbent core 50 of the present invention preferably have a number average cell size of from about 30 to about 130 μm. The cells in such substantially open-celled foam structures have intercellular openings or holes that provide passageways large enough to permit free and ready movement of blood and blood-based liquids, such as menses, from one cell to another within the foam structure, even though these liquids contain certain insoluble components. These substantially open-celled foam structures will generally have a reticulated character with the individual cells being defined by a plurality of mutually connected, three dimensionally branched webs. Cell size is a foam parameter that can impact a number of important mechanical and performance features of the absorbent foams used in the present invention. Cell size contributes to capillary suction specific surface area (CSSA), together with foam hydrophilicity, determines the capillarity of the foam. Therefore, cell size is a foam structure parameter that can directly affect the fluid wicking properties of absorbent foams, as well as the capillary pressure that is developed within the foam structure. A number of techniques are available for determining the cell size of foams. The most useful technique for determining cell size in foams involves a simple measurement based on the scanning electron photomicrograph of a foam sample. Superimposing a scale on a photomicrograph of the foam structure can be used to determine average cell size via visual inspection or an image analysis procedure. Foam cells, and especially cells that are formed by polymerizing a monomer-containing oil phase that surrounds relatively monomer-free water-phase droplets, will frequently be substantially spherical in shape. The size or "diameter" of such spherical cells is a commonly used parameter for characterizing foams in general. Since cells in a given sample of polymeric foam will not necessarily be of approximately the same size, an average cell size, i.e., number average cell diameter, will often be specified.

The cell size of the foam comprising the acquisition/fit portion 54 is preferably greater than that of the foam comprising the storage portion 56. Preferably, the cell size of the acquisition/fit portion 54 (expressed in terms of number average cell diameter or mean cell diameter) ranges between about 100–130 microns and the cell size of the storage portion 56 preferably ranges between about 35–60 microns. The larger cell size provides the acquisition/fit portion 54 with the ability to acquire blood-based liquids at a higher rate by allowing red blood cells, debris, and other liquids to be taken into the acquisition/fit portion 54. The difference in cell size between the acquisition/fit portion 54 and the storage portion 56 establishes a capillary gradient from the acquisition/fit portion 54 to the storage portion 56. This will cause liquids to move from the acquisition/fit portion 54 into the storage portion 56. The movement of liquids out of the acquisition/fit portion 54 will drain the acquisition/fit portion 54 to make room in the acquisition/fit portion 54 for subsequent loading of liquids. In addition, the capillary gradient will also ensure that liquids which are transported to the storage portion 56 will remain in the storage portion 54, and will not tend to go back up into the acquisition/fit portion 54. The storage portion 56 develops higher capillary pressure, but will generally accept menstrual liquids at a slower rate than the acquisition/fit portion 54.

Another feature useful in defining these preferred foams is hole size. The holes are the openings between adjacent cells that maintain liquid communication between these cells. The foams used in the present invention have hole sizes sufficiently large to allow passage of the insoluble components of blood, especially the red blood cells, to avoid blockage of these liquid passages. The preferred technique for determining hole size is image analysis based on scanning electron micrographs of the foams as discussed above. The foams used in the present invention preferably have a number average hole size of from about 5 μm to about 30 μm, and preferably from about 10 to about 27 μm. While foams having hole sizes larger than about 30 μm will allow passage of blood cells, they will generally not have the fine microstructure necessary to provide the fluid capillary absorbent pressure of the foams useful in the present invention.

It may also be more desirable and preferable to alternatively express the difference in the foam properties of the acquisition/fit portion 54 and the storage portion 56 in terms of "capillary specific surface area"("CSSA") since such a measurement may more accurately correlate with the liquid handling properties of the two portions of the absorbent core 50. The capillary specific surface area is one of a number of characteristics important to absorbing and transporting blood and blood-based liquids. "Capillary specific surface area" is a measure of the test-liquid-accessible surface area of the polymeric network accessible to a test liquid. Capillary specific surface area is determined both by the dimensions of the cellular units in the foam and by the density of the polymer comprising the foam. It is, thus, a way of quantifying the total amount of solid surface provided by the foam network to the extent that such a surface participates in absorbency. The capillary specific surface area is determined by the method set forth in the TEST METHODS section deleting of this specification.

Generally, the CSSA of the foam at a constant volume increases as the cellular structure becomes smaller celled (or "finer"). Higher surface areas are highly desirable to develop the capillary pressure needed to attract liquids such as menses away from the body. However, the surface area of the foam can reach the point that the rate of liquid absorption becomes limiting, as well as increasing the likelihood that insoluble components within the liquid can no longer pass readily from one cell to another. Accordingly, the surface area of the foam needs to be selected within a particular range to balance these competing factors. Polymeric foams that are useful in the foam absorbent core of the present invention are those that have a capillary specific surface area in the range of from about 0.0080 to about 0.040 $m^2/cc$. Typically, the capillary specific surface area is in the range from about 0.010 to about 0.030 $m^2/cc$, preferably from about 0.012 to about 0.026 $m^2/cc$.

The upper acquisition/fit portion 54 (facing the body of the wearer) preferably has a lower capillary specific surface area than the storage portion 56. For example, the acquisition/fit portion 54 may have a CSSA of from about 0.012 to about 0.020 $m^2/cc$. The storage portion 56 may have a capillary suction specific surface area, for example, of from about 0.020 to about 0.026 $m^2/cc$. In this way, the storage portion 56 will have a higher capillary pressure, allowing it to drain liquids from the upper acquisition/fit portion 54, thus keeping the body of the wearer relatively free from contact with liquids.

The foams must be suitably resistant to deformation or compression by forces encountered when such absorbent foams are engaged in the absorption and retention of liquids. The resistance to compression deflection (or "RTCD") exhibited by the polymeric foams used in the present invention can be quantified by determining the amount of strain (percentage of uncompressed height) produced in a sample of saturated foam held under a certain pressure for a specified period of time. The method for carrying out this particular type of test is described in the TEST METHODS section of U.S. Pat. No. 5,387,207, issued to Dyer, et al. Foams useful as absorbent members for catamenial products are those which exhibit a RTCD such that a confining pressure of 0.74 psi (5.1 kPa) at 31° C. after 15 minutes produces a strain of typically from about 5 to about 85% compression of the foam structure.

The acquisition/fit portion 54 can be more easily compressible (that is, less resistant to compression (or higher "RTCD")) than the storage portion 56. This will allow the acquisition/fit portion 54 to compress to fit comfortably in the space between the wearer's labia and gluteal groove. It is estimated that the acquisition/fit portion 54 will not deform the wearer's labia if it has a resistance to compression deflection that is between about 40% and about 85%. The storage portion 56 does not need to be as compressible since it underlies the acquisition/fit portion 54 and is not in as close proximity to the wearer's body. In addition, the higher resistance to compression of the storage portion 56 reduces any tendency for liquids to be "squeezed" out of the storage portion. The acquisition/fit portion 54 may, for example, have a resistance to compression of between about 60% to about 85%, and more preferably between about 65% to about 75%. The storage portion 56 may, in such a case, have a resistance to compression of between about 5% to about 50%, and more preferably between about 10% to about 35%.

The foams used in the absorbent structure are preferably also resilient so that they do not permanently collapse after compression. This will ensure that the foams are able to continue to absorb bodily exudates after compression. The resilient characteristics of the foams also ensures that the primary absorbent component will be capable of continuing to conform to and fill the space between the wearer's labia and gluteal groove after initial compression and after changes in the configuration of these parts of the wearer's body caused by body movements. Preferably, the foams used in the absorbent structure will return to at least about 70% of their uncompressed height, more preferably at least about 80%, and most preferably at least about 90% after the removal of the compressive forces.

Another important property of absorbent foams used in the present invention is their free absorbent capacity. For absorbent members useful in catamenial products, free absorbent capacity is the total amount of test liquid (i.e., synthetic urine) that a given foam sample will absorb at equilibrium into its cellular structure per unit mass of solid material in the sample. The foams that are especially useful as absorbent members in catamenial products will at least meet a minimum free absorbent capacity. The free absorbent capacity of the foams used in the present invention can be determined using the procedure described in the TEST METHODS section of U.S. Pat. No. 5,387,207 issued to Dyer, et al. To be especially useful as absorbent members for catamenial products, the foams used in the present invention should have a free absorbent capacity of from about 20 to about 125 g/g, preferably from about 25 to about 60 g/g, and most preferably about 35 g/g, of synthetic urine per gram of dry foam.

It should be understood that these foams can have different properties, features and/or characteristics at different times prior to contact between the foam and the blood or blood-based liquid to be absorbed. For example, during their manufacture, shipping, storage, etc., these foams can have density and/or cell size values outside the ranges set forth hereafter for these parameters, for example if they are stored in a compressed state by packaging. However, such foams are nevertheless still within the scope of this invention if they later undergo physical changes so that they have the requisite values specified hereafter for these properties, features and/or characteristics at least some point prior to and/or during contact with the blood or blood-based liquid to be absorbed.

FIG. 2 shows one preferred arrangement of the acquisition/fit portion 54 and storage portion 56. In FIG. 2, the core 50 comprises a plurality of foam pieces that provide the preferred body fitting shape of the primary absorbent member 40. In one preferred embodiment, as shown in FIG. 2, the foam pieces are in the shape of elongated parallelepipeds. In this embodiment, the acquisition/fit portion 54 and storage portion 56 comprise separate components comprising rectangular strips of foam that have a rectangular cross-section. The strip of foam forming the acquisition/fit portion 54 preferably measures about 0.5 cm in height by about 8–10 inches (about 20–25.4 cm), preferably about 9 or 10 inches (about 23–25.4 cm) in length, and about 0.25 inches (about 0.64 cm) in width. The foam comprising the acquisition/fit portion 54 preferably has a cell size in the range of between about 100 microns to about 130 microns, a capillary specific surface area of about 0.014 to about 0.020 m2/cc, and a resistance to compression of about 60% to about 85%.

The storage portion 56 comprises a separate component comprising one or more rectangular strips of foam that also have a rectangular cross-section. Preferably, the storage portion 56 comprises two or three strips of foam. In the preferred embodiment shown in FIG. 2, the storage portion 56 comprises three rectangular strips of foam. The strips of foam forming the storage portion 56 preferably measure about 0.5 cm in height by about 8–10 inches (about 20–25.4 cm) in length, and are preferably about 9 or 10 inches long. The strips forming the storage portion 56 can all be the same length, or they can decrease in length from the bottom strip to the top strip. The strips comprising the storage portion 56 preferably have widths of about 0.5 inches (about 1.3 cm) for the uppermost strip, about 0.75 inches (about 2 cm) for the underlying strip, and about 1 inch (about 2.54 cm) for the lowermost strip. The three strips forming the storage portion 56 preferably have the same composition and characteristics. In alternative embodiments, however, properties and/or composition of the foam in the strips making up the storage portion 56 can be varied. For example, capillary specific surface area could be varied to establish a capillary gradient with the storage portion 56. The foam comprising the storage portion 56 preferably has a cell size in the range of between about 35 microns to about 60 microns, a capillary specific surface area of between about 0.020 to about 0.026 m$^2$/cc, a resistance to compression of about 10 to about 35%.

The strips of foam comprising the acquisition/fit portion 54 and the storage portion 56 may be secured in the stacked arrangement shown in the drawings in any suitable manner. Preferably, the strips of foam are wrapped by a nonwoven web wrapper or acquisition layer 58 to retain the integrity of the stacked structure. A preferred nonwoven material for this purpose is an 18 g/yd$^2$ (21.5g/m$^2$) spunbonded polypropylene nonwoven material known as CELESTRA available from Fiberweb, North America of Simpsonville, S.C., which is then embossed with the pattern described in U.S. Pat. No. 4,781,710 issued to Megison, et al. on Nov. 1, 1988 known as P9. The wrapper 58 may, but need not be, secured to the strips of foam. Preferably, the wrapper 58 is simply wrapped around the foam and secured to itself, and is not secured to the strips of foam.

b. Preparation of the Polymeric Foam for the Absorbent Core

The process for preparing the polymeric foam for the absorbent core is important to ensuring that the foam absorbs blood and blood-based liquids, and has the desired characteristics for use in the acquisition/fit portion 54 and the storage portion 56. Foam preparation involves the steps of: 1) forming a specific type of stable high internal phase water-in-oil emulsion (or HIPE) having a relatively small amount of an oil phase and a relatively greater amount of a water phase; 2) polymerizing/curing this stable emulsion under conditions suitable for forming a solid water-filled polymeric foam structure; 3) slicing or otherwise cutting the water-filled polymeric foam and then washing the sliced or cut foam to remove the original residual water phase, and especially the residual hydratable salts, from the polymeric foam structure; 4) treating the polymeric foam structure with a hydrophilizing solution of surfactant and salt; and thereafter dewatering this polymeric foam structure.

The first step is forming a specific type of stable high internal phase water-in-oil emulsion (or HIPE) having a relatively small amount of an oil phase and a relatively greater amount of a water phase. The water-in-oil emulsion is formed from an oil phase and a water phase. The oil phase comprises from about 85 to about 98% by weight of a monomer component and from about 2 to about 15% by weight of an emulsifier component. The monomer component is capable of forming a copolymer having a Tg of about 50° C. or lower. The "Tg" of a copolymer is its glass transition temperature. The emulsifier component is soluble in the oil phase and is suitable for forming a stable water-in-oil emulsion. The water phase comprises an aqueous solution containing from about 0.2 to about 20% by weight of a water-soluble electrolyte. The volume to weight ratio of water phase to oil phase is in the range of from about 20:1 to about 125:1.

The monomer component of the oil phase comprises: (i) from about 45 to about 70% by weight of at least one substantially water-insoluble monofunctional monomer capable of forming an atactic amorphous polymer having a Tg of about 35° C. or lower; (ii) from about 10 to about 40% by weight of at least one substantially water-insoluble monofunctional comonomer capable of imparting toughness about equivalent to that provided by styrene; (iii) from about 5 to about 25% by weight of a first substantially water-insoluble, polyfunctional crosslinking agent selected from divinyl benzenes, trivinyl benzenes, divinyl toluenes, divinyl xylenes, divinyl naphthalenes divinyl alkylbenzenes, divinyl phenanthrenes, divinyl biphenyls, divinyl diphenylmethanes, divinyl benzyls, divinyl phenylethers, divinyl diphenylsulfides, divinyl furans, divinyl sulfide, divinyl sulfone, and mixtures thereof, and (iv) from 0 to about 15% by weight of a second substantially water-insoluble, polyfunctional crosslinking agent selected from polyfunctional acrylates, methacrylates, acrylamides, methacrylamides, and mixtures thereof. The percentages shown as range for crosslinkers and monomers above are expressed on a 100% basis. For example, if a crosslinker is provided as a 50% mixture with another compound, the percentage used in the ranges above refers to 50% of the actual amount of that chemical mixture used.

The emulsion component of the oil phase comprises: (i) a primary emulsifier having at least about 40% by weight emulsifying components selected from diglycerol monoesters of linear unsaturated $C_{16}$–$C_{22}$ fatty acids, diglycerol monoesters of branched $C_{16}$–$C_{24}$ fatty acids, diglycerol monoaliphatic ethers of branched $C_{16}$–$C_{24}$ alcohols, diglycerol monoaliphatic ethers of linear unsaturated $C_{16}$–$C_{22}$ alcohols, diglycerol monoaliphatic ethers of linear saturated $C_{12}$–$C_{14}$ alcohols, sorbitan monoesters of linear unsaturated $C_{16}$–$C_{22}$ fatty acids, sorbitan monoesters of branched $C_{16}$–$C_{24}$ fatty acids, and mixtures thereof; or (ii) the combination a primary emulsifier having at least 20% by weight of these emulsifying components and certain secondary emulsifiers. Preferred secondary emulsifiers are ditallow dimethyl ammonium methyl sulfate and ditallow dimethyl ammonium methyl chloride. When these optional secondary emulsifiers are included in the emulsifier component, it is typically in a weight ratio of primary to secondary emulsifier of from about 50:1 to about 1:4.

The water-in-oil emulsion is preferably formed at a temperature of about 50° C. or higher under low shear mixing. The individual components used to form the emulsion are described in greater detail below.

Emulsion of the oil and water phase combination will frequently involve the use of a mixing or agitation device such as a pin impeller. Shear mixing (or shear agitation) is generally performed to the extent and for a time period necessary to form a stable emulsion. A preferred continuous process for forming a HIPE is described in greater detail in U.S. Pat. No. 5,149,720 issued to DesMarais, et al.

The monomer component is then polymerized in the oil phase of the water-in-oil emulsion to form a polymeric foam material. The HIPE formed will generally be collected or poured into a suitable reaction vessel, container or region to be polymerized or cured. In one embodiment, the reaction vessel comprises a tub constructed of polyethylene from which the eventually polymerized/cured solid foam material can be easily removed for further processing after polymerization/curing has been carried out to the extent desired. It is usually preferred that the temperature at which the HIPE is poured into the vessel be approximately the same as the polymerization/curing temperature.

Suitable polymerization/curing conditions will vary depending upon the monomer and other makeup of the oil and water phases of the emulsion (especially the emulsifier systems used), and the type and amounts of polymerization initiators used. Frequently, however, suitable polymerization/curing conditions will involve maintaining the HIPE at elevated temperatures above about 50° C. for about 18 hours.

A porous water-filled open-celled HIPE foam is typically obtained after polymerization/curing in the reaction vessel. The solid polymerized HIPE foam will generally be filled with residual water phase material used to prepare the HIPE. This residual water phase material (generally an aqueous solution of electrolyte, residual emulsifier, and polymerization initiator) should be at least partially removed prior to further processing and use of the foam. This polymerized HIPE foam is typically cut or sliced into a sheet-like form. Sheets of polymerized HIPE foam are easier to process during subsequent treating/washing and dewatering steps, as well as to prepare the HIPE foam for use in absorbent articles. The polymerized HIPE foam is typically cut/sliced to provide a cut thickness in the range of from about 0.8 to about 10 mm, preferably from about 1 to about 5 mm. These sheets are dewatered by compressing the foam structure to squeeze out residual liquid and/or by washing the foam structure with water or other aqueous washing solutions. Frequently several compressing and washing steps, e.g., from 2 to 4 cycles, will be used.

Following this, the water-filled polymeric foam material is sliced or otherwise cut and then washed to lower the level of residual electrolytes less than about 2%. The removal of most of the residual electrolyte (i.e., hydratable salts) from the foam is particularly important. As noted previously, these hydratable salts are typically included during initial formation of the HIPE to minimize the tendency of monomers, comonomers, and crosslinkers that are primarily oil soluble to also dissolve in the water phase. However, after polymerization of the HIPE, the presence of these salts is unnecessary and can adversely affect the ability of the foam to absorb blood and blood-based liquids such as menses, especially as the concentration of these salts in the foam increases. Accordingly, it desirable to reduce the level of these hydratable salts in the foam during this washing step. After washing, the foams of the present invention have less than about 2% of such residual hydratable salts. Preferably, the foams of the present invention have less than about 0.5% of such residual salts, more preferably between about 0.01% and about 0.15%, and most preferably between about 0.03% and about 0.12% as calcium chloride by weight of the dry foam.

The washed foam is then treated with an effective amount of a suitable hydrophilizing surfactant. The treatment of the washed foam with a hydrophilizing surfactant is generally needed to render the foam relatively more hydrophilic so that the foam will be useful as absorbents for blood and blood-based liquids such as menses. The hydrophilizing surfactants used in the process of making the foam can be any material that enhances the water wettability of the polymeric foam surface. Suitable surfactants should be non-toxic and non-irritating to mucus membranes. The surfactants should be soluble or dispersible in warm water. Preferably, the hydrophilizing surfactant is a liquid at temperatures near ambient for ease of incorporation during the foam making process. A particularly preferred surfactant is PEGOSPERSE 200 ML sold by Stepan Chemical Corp., Northfield, Ill., an ethoxylate of lauric acid having an average of 4.5 ethoxy units. The surfactant is preferably combined with about 0.05% aqueous $CaCl_2$.

The hydrophilizing surfactant can be dissolved or dispersed in a hydrophilizing solution that is applied to the HIPE foam surface. In this manner, hydrophilizing surfactants can be adsorbed by the preferred HIPE foams in amounts suitable for rendering the surfaces thereof substantially hydrophilic, but without substantially impairing the desired flexibility and compression deflection characteristics of the foam. Treatment of the HIPE foam with the hydrophilizing surfactant continues until the foam exhibits the desired degree of wettability. In preferred foams, the hydrophilizing surfactant is incorporated such that residual amounts of the surfactant that remain in the foam structure are typically in the range from about 0.1% to about 5%, preferably from about 0.2% to about 1%, by weight of the foam.

The washed foam is then dewatered to a moisture content of about 40% or less. Dewatering can be achieved by compressing the foam (preferably in the z-direction) to squeeze out residual water, by subjecting the foam and the water therein to temperatures of from about 60° to about 200° C. or to microwave treatment, by vacuum dewatering or by a combination of compression and thermal drying/microwave/vacuum dewatering techniques. The dewatering step will generally be carried out until the HIPE foam is ready for use and is as dry as practicable. Frequently such compression dewatered foams will have a water (moisture) content of from about 50 to about 500%, more preferably from about 50 to about 200%, by weight on a dry weight basis. Subsequently, the compressed foams can be thermally dried to a moisture content of about 40% or less, preferably in the range of from about 5 to about 15%, on a dry weight basis.

After the HIPE foam has been dewatered, it can be slitted in various patterns. These include patterns that conform to the shape of the catamenial product in which the slitted foam is used as an absorbent member.

The preparation of the foams suitable for use in the absorbent article of the present invention is described in greater detail in allowed U.S. patent application Ser. No. 08/542,497 (P&G Case 5546R) entitled "Foams Made From High Internal Phase Emulsion Useful as Absorbent Members for Catamenial Pads", filed in the name of Dyer on Oct. 13, 1995.

EXAMPLE 1

HIPE Preparation:

An aqueous phase is prepared containing the ingredients shown in Table 1. The oil phase is prepared using the ingredients shown in Table 2.

TABLE 1

Aqueous Phase Composition for HIPE.

| | | |
|---|---|---|
| Water | 756 L | |
| Potassium Persulfate | 378 g | 0.05% |
| Calcium Chloride | 72,640 g | 10.0% |

TABLE 2

"Oil Phase" Composition for HIPE.

| | | |
|---|---|---|
| 2-ethylhexyl acrylate | 3,000 g | 50% |
| styrene | 600 g | 10% |
| divinyl benzene* | 2,400 g | 40% |
| diglycerol monooleate | 360 g | 6%** |
| Tinuvin 765 | 30 g | 0.5%** |

*Divinyl benzene in this table is a special blend comprising 61% ethyl styrene and 39% divinyl benzene, unless otherwise specified.
**Addition level of emulsifier and other adjuvants to the oil phase are "add-on" percentages; monomer composition sums to 100%. The 6% of emulsifier is actually 6 parts per 106 parts.

In Table 2, Tinuvin 765 is bis(1,2,2,5,5-pentamethylpiperidinyl)sebacate, a product of Ciba-Geigy Corp. This diglycerol monooleate emulsifier is prepared following the general procedure for preparing polyglycerol esters described in U.S. Pat. No. 5,387,207 (Dyer et al.) issued Feb. 7, 1995.

Controlled ratios of the oil phase stream (25° C.) and water phase are fed to a dynamic mixing apparatus, described in more detail in U.S. Pat. No. 5,387,207 (Dyer et al.) issued Feb. 7, 1995. Appropriate mixing of the combined streams in the dynamic mixing apparatus is achieved by means of pin impellers in mixing cylinders. The HIPE so made is poured into a vessel, typically a round polypropylene tub, 17 in. (43 cm) in diameter and 7.5 in. (10 cm) high, with a concentric insert made of Celcon plastic which is rotating beneath the exit nozzles of the mixing chamber. The insert is 5 in. (12.7 cm) in diameter at its base and 4.75 in (12 cm) in diameter at its top and is 6.75 in. (17.14 cm) high. The vessel is filled to about 0.5 inches from the top and the polymer is cured in a room maintained at 65° C. for about 18 hours.

Table 3 summarizes the conditions under which each HIPE stream was made along with relevant properties of the foams produced from these HIPE streams following curing. In both cases, the HIPEs are produced at a rate of 5.1 lb./min. The result after polymerizing is sliced continuously and dewatered to give foams 5 mm thick. Dewatering comprises passing the sliced sheets of foam over four successive vacuum dewatering nip rollers with intermediate resaturation with an aqueous solution of 0.5% Pegosperse 200 ML and 0.05% calcium chloride. After the final nip roll, the foam is dried thermally.

TABLE 3

Preparative Conditions and Properties of Foams A and B.

| Property | Foam A | Foam B |
|---|---|---|
| Water:Oil Ratio | 43 | 37 |
| Mixer RPM | 400 | 600 |
| Pour Temperature | 66° C. | 66° C. |
| Tg | 28° C. | 28° C. |
| RTCD | 60% | 20% |
| Free Absorbent Capacity | 40 g/g | 35 g/g |

TABLE 3-continued

Preparative Conditions and Properties of Foams A and B.

| Property | Foam A | Foam B |
|---|---|---|
| Density* | 0.022 g/cc | 0.026 g/cc |
| Mean Cell Diameter | 120 μm | 50 μm |
| Portion in Product | Acquisition/Fit 54 | Storage 52 |

*Density in this and all following examples is measured on foams washed in water and 2-propanol to remove residual salts and wetting agents.

EXAMPLE 2

In a separate experiment, a HIPE is prepared as in Example 1 using the oil phases shown in Table 4 and mixing conditions and properties shown in Table 5 to prepare Foams C and D. (The aqueous phase is the same as in Table 1.)

TABLE 4

"Oil Phase" Composition, Mixing Conditions, and Properties.

| | Foam C | Foam D |
|---|---|---|
| 2-ethylhexyl acrylate | 55% | 50% |
| styrene | 0% | 0% |
| divinyl benzene* | 45% | 50% |
| diglycerol monooleate | 6%** | 6%** |
| Tinuvin 765 | 0.5%** | 0.5%** |

*Divinyl benzene in this table is a special blend comprising 66% ethyl styrene and 34% divinyl benzene.
**Addition level of emulsifier and other adjuvants to the oil phase are "add-on" percentages; monomer composition sums to 100%. The 6% of emulsifier is actually 6 parts per 106 parts.

TABLE 5

Preparative Conditions and Properties of Foams C and D.

| Condition or Property | Foam C | Foam D |
|---|---|---|
| Mixing RPM | 400 | 800 |
| Pour Temperature | 60° | 50° |
| Pour Rate | 5.1 lb./min | 5.1 lb. min. |
| W:O Ratio | 45:1 | 40:1 |
| Free Absorbent Capacity | 43 g/g | 38 g/g |
| Density | 0.022 g/cc | 0.024 g/cc |
| Mean Cell Diameter | 120 μm | 40 μm |
| RTCD | 70% | 30% |
| Tg | 12° C | 22° C |
| Portion in Product | Acquisition/Fit 54 | Storage 56 |

The HIPEs so produced are processed as in Example 1. Foam C is used for the acquisition/fit portion 54 and Foam D is used for the storage portion 56.

EXAMPLE 3

The HIPE streams used to make Foam A and Foam B described in Example 1 are delivered to the receiving vessel at the same rate via separate mixing nozzles and having been prepared using different conditions of temperature and dynamic mixing. This produces a foam having microstructural heterogeneity while having identical chemical composition and water:oil ratios. In a specific example, both streams are mixed at a water-to-oil ratio of 50:1. Emulsion E is produced using the dynamic pin mixer rotating at 1200 rpm at a delivery rate of 6.0 lb/min. into the tub turning at 2 rpm. Emulsion F is produced using the dynamic pin mixer rotating at 400 rpm at a delivery rate of 6.0 lb./min. into the opposite side of the same tub. When cured and sliced as described hereinabove, this produces a foam wherein the different regions have and densities of 0.20 g/cc but different regions within the foam having different cell sizes consistent with the acquisition/fit and storage portions discussed herein.

In another embodiment, the two streams may be collected in a continuous trough having the dimensions of the product described hereinabove wherein the Emulsion E composition fills the upper flat portion of the trough and Emulsion F composition fills the lower shaped portion of the trough. This results, after appropriate curing, washing, and dewatering, in a heterogeneous foam in one piece expressing the properties desired.

The absorbent structure used in the present invention differs from prior absorbent structures in several ways. Prior absorbent structures have utilized separate components to provide the structure with the desired absorbency and resiliency. This produced the disadvantages that the different components might interfere with each other. For instance, structures that used a resilient component for fit typically required that an absorbent component be placed on top of the resilient component because the resilient component would not provide adequate acquisition and absorbency, particularly in heavy flow situations. This, however, would create additional bulk that would interfere with the body conformity and fit of the resilient component. The more absorbent material that is added to increase capacity, the more negatively this would impact body conformity and fit. Thus, it is desirable to have high capacity for absorbency, but without a lot of uncomfortable bulk.

The components of the absorbent core 50 used in the present invention provide the sanitary napkin 20 with absorbency and fit while being fully compatible with each other. The acquisition/fit portion 54 is able to easily take in body exudates such as urine and menses. In addition, it is compressible, yet resilient, so that it fits comfortably closely against the wearer's body and conforms to the contours of the wearer's body. The storage portion 56 takes absorbed liquids from the acquisition/fit portion 54 and stores those liquids.

The absorbent structure used in the sanitary napkin of the present invention provides numerous advantages. The absorbent structure described herein is comprised of a foam material that is especially suitable for handling absorbing, and storing blood-based liquids such as menses. The entire absorbent structure is absorbent and resilient so that it does not require the presence of a separate resilient component that would interfere with the overall absorbency of the absorbent structure. The absorbent structure is highly compressible so that it can be compressed to a relatively small size to fit comfortably in the space between the wearer's labia, or it can occupy the relatively large area in the wearer's gluteal groove. The fit of the sanitary napkin in the wearer's gluteal groove has been found to be particularly important in preventing leakage from the rear of the sanitary napkin during night time usage of the sanitary napkin when the wearer is lying down. Further, because of its material composition, geometry, and compressibility, the absorbent structure, unlike the majority of prior absorbent structures with raised elements thereon, can routinely and comfortably achieve an interlabial fit on wearers having a wide variety of body dimensions.

B. The Secondary Absorbent Member.

The second main component of the compound sanitary napkin embodiment shown in FIGS. 1–3, is the secondary absorbent member 60. The secondary absorbent member 60 primarily functions to protect the user's garments from soiling by absorbed fluids which may be expelled from the primary absorbent member 40 or which may inadvertently bypass the primary absorbent member 40. Thus, the secondary absorbent member 60 generally performs a different function from that of the primary absorbent member 40 and is preferably somewhat thinner and less bulky than the primary absorbent member 40.

The secondary absorbent member 60 can be of any suitable plan view shape and size. For instance, the plan view shape of the secondary absorbent member 60 can include but not be limited to generally rectangular, oval, hourglass, dog-bone, asymmetric and other shapes that are known in the art. In the embodiment shown in FIGS. 1–3, the secondary absorbent member 60 is preferably generally hourglass-shaped. The width of the secondary absorbent member 60 is preferably at least 1.5 times the width of the primary absorbent member 40. More preferably, the width of the secondary absorbent member 60 is at least 2 times the width of said primary absorbent member 40. Most preferably, the width of the secondary absorbent member 60 is in the range from about 3 to about 8 times the width of the primary absorbent member 40.

The secondary absorbent member 60 can be of any thickness, including relatively thick, intermediate (or moderate) thickness, relatively thin, or even very thin or "ultra thin". In the embodiment shown, the secondary absorbent member 60 is preferably very thin and flexible or "ultra thin". The secondary absorbent member 60 preferably has a caliper of less than about 3.0 millimeters, more preferably less than about 2.6 millimeters, even more preferably less than about 2.2 millimeters, and most preferably less than about 2.0 millimeters. Examples of sanitary napkins that could serve as the secondary abosrbent member 60 are described in U.S. Pat. Nos. 4,950,254 and 5,009,653 issued to Osborn.

The secondary absorbent member 60, however, may also have significantly less absorbent capacity than the primary absorbent member 40. For example, the secondary absorbent member 60 may have a total capacity of of between about 5–15 grams of bodily exudates. Preferably, the ratio of the total capacity of the primary absorbent member 40 to the total capacity of the secondary absorbent member 60 is between about 1:1 and about 10:1, and more preferably, is about 5:1.

The secondary absorbent member 60 preferably comprises at least two components. They comprise an absorbent element 62 and a liquid impervious backsheet 66 joined to the absorbent element 62. The absorbent element 62 may form the body contacting surface 60A of the secondary absorbent member 60. In other preferred embodiments, the secondary absorbent member 60 may comprise a liquid impervious backsheet 66, a liquid pervious topsheet 64 joined to the backsheet 66, and the absorbent element 62 may be positioned between the topsheet 64 and the backsheet 66. In yet other embodiments, the secondary absorbent member 60 may comprise an acquisition layer 68 in addition to or in place of the topsheet 64. These components of the secondary absorbent member 60 will now be examined in greater detail.

The topsheet 64 can be any liquid pervious material commonly used in sanitary napkins, disposable diapers, and the like. The topsheet 64 can be any of the materials described above as being useful in the outer cover 52 of the primary absorbent member 40, including, but not limited to nonwovens and apertured formed films.

The acquisition layer 68 of the secondary absorbent member 60 may comprise any of the materials described above with regard to the acquisition layer 58 of the primary absorbent member 40. In preferred embodiments, the secondary absorbent member 60 comprises an acquisition layer 68 disposed between the topsheet 64 and the absorbent element 62. However, embodiments are contemplated wherein the acquisition layer 68 replaces the topsheet 64, the absorbent element 62 or both. In such configurations, the acquisition layer 68 provides any absorption characteristics desired in the secondary absorbent member 60.

The absorbent element 62 may be manufactured from a wide variety of liquid absorbent materials commonly used in disposable sanitary napkins, and other disposable absorbent articles. Examples of suitable absorbent materials include comminuted wood pulp, which is generally referred to as airfelt; creped cellulose wadding, modified cross-linked cellulose fibers such as those described in U.S. Pat. No. 5,217,445 issued to Young, et al. on Jun. 8, 1993; capillary channel fibers (fibers having intra-fiber capillary channels such as those described in U.S. Pat. No. 5,200,248 issued to Thompson, et al. on Apr. 6, 1993); absorbent foams such as those described in U.S. Pat. No. 5,260,345, issued to DesMarais, et al. on Nov. 9, 1993; U.S. Pat. No. 5,268,244 issued to DesMarais, et al. on Dec. 7, 1993; U.S. Pat. No. 5,331,015 issued to DesMarais et al., on Jul. 19, 1994; and U.S. Pat. No. 5,387,207 issued to Dyer et al., on Feb. 7, 1995); thermally bonded airlay materials such as those material described in U.S. patent application Ser. No. 08/141,156, entitled "Catamenial Absorbent Structures Having Thermally Bonded Layers For Improved Handling of Menstrual Fluids and Their Use In Catamenial Pads Having Improved Fit and Comfort" filed in the name of Richards, et al. on Oct. 21, 1993 (P&G Case 5051); polyurethane, absorbent sponges; synthetic staple fibers; polymeric fibers; hydrogel-forming polymer gelling agents ("absorbent gelling materials"); peat moss; glass fibers or any equivalent materials or combinations of materials. In addition, since the absorbent capacity requirements of the secondary absorbent member may be relatively low, the absorbent element 62 may comprise any of the materials described above as being useful in the acquisition layers 58 and 68. For this, paper tissue (either single or multiple plies) is also suitable for use in the absorbent element 62.

In one preferred embodiment, the absorbent element 62 is formed of from about 1 to about 5 plies of paper tissue. Paper tissue comprising one or more plies having a basis weight of from about 24 to about 48 grams per square meter and an apparent density of from about 0.10 to about 0.12 grams per cubic centimeter as made by the process described in U.S. Pat. No. 3,301,746 issued to Sanford, et al. on Jan. 31, 1967, has been found to be quite satisfactory for use as the absorbent element 62. Paper tissue made by the process described in U.S. Pat. No. 3,994,771 issued to Morgan, et al. on Nov. 30, 1976, can also be used to good advantage as the absorbent element 62. Wet strength resins and latex binders can be, and preferably are, used to provide additional strength to the paper tissue used in the absorbent element 62.

The backsheet 66 of the secondary absorbent member 60 is preferably impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. In use, the backsheet 66 is interposed between the absorbent element 62 and the user's undergarments. The function of the backsheet 66 is to prevent exudates which may be expelled from or which inadvertently bypass the absorbent core 50 and exudates absorbed and contained in the absorbent element 62 from contacting and soiling the user's undergarments.

The backsheet 66 may comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.015 mm (2.0 mil). Exemplary polyethylene films are manufactured by Clopay Corporation of Cincinnati, Ohio under the designation P18-0401 and microflex 1401. The backsheet is preferably embossed and/or matte finished to provide a more clothlike appearance. Further, the backsheet may permit vapors to escape from the absorbent element 62 (i.e., breathable) while still preventing exudates from passing through the backsheet.

The topsheet 64, the backsheet 66, and the absorbent element 62 may be assembled in a variety of configurations known in the art (including so called "sandwich" products and "tube" products). Several preferred sanitary napkin configurations and features that the sanitary napkin can be provided with are described generally in the following patents: U.S. Pat. No. 4,321,924, "Bordered Disposable Absorbent Article" issued to Ahr on Mar. 30, 1982; U.S. Pat. No. 4,425,130 issued to DesMarias on Jan. 10, 1984; U.S. Pat. Nos. 4,950,264 and 5,009,653, both entitled "Thin, Flexible Sanitary Napkin" issued to Osborn on Aug. 21, 1990 and Apr. 23, 1991, respectively; and U.S. Pat. Nos. 5,234,422 and 5,308,346 issued to Sneller, et al.

The components of the secondary absorbent member 60, as shown in FIGS. 1–3, are preferably assembled in a sandwich construction in which the topsheet 64 and the backsheet 66 have dimensions that are generally larger than those of the absorbent element 62. The topsheet 64 is joined to the acquisition layer 68. The topsheet 64 is joined to the backsheet 66 in the region of the sanitary napkin that lies outboard of the absorbent element 62. Preferably, the topsheet 64 is joined to these components by a core bonding adhesive that is applied in a spiral pattern. The absorbent element 62 is preferably joined to the backsheet 66. Preferably, the absorbent element 62 and the backsheet 66 are joined using a core integrity adhesive applied in a plurality of strips of adhesive, each of which comprises spirals of adhesive. Exemplary means for joining these components of the secondary absorbent member 60 comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. The core integrity adhesive can be applied over the entire garment facing side of the secondary absorbent, over the whole product width (including the extensions of the backsheet that will lie beyond the edges of the absorbent element 62) or any portion thereof. Preferably, the core integrity adhesive is applied to the entire interface between the garment facing side of the topsheet 64 and the backsheet 68.

To form the compound sanitary napkin of the present invention, the primary absorbent member 40 and the secondary absorbent member 60 are joined by union means generally indicated as 70 in FIGS. 1 and 2. The precise nature of the union means is immaterial so long as the union means selected serves to join the primary absorbent member 40 and the secondary absorbent member 60 into the compound sanitary napkin 20 of the present invention with sufficient tenacity that the primary absorbent member 40 and the secondary absorbent member 60 are not disconnected during use. Union means such as adhesive attachment with well known hot melt and pressure sensitive adhesives are quite satisfactory. If the nature of the components selected to construct the constituents of the compound sanitary napkin 20 so permit, heat welding, ultrasonic welding, dynamic mechanical bonds or a combination of any of the above-mentioned means can be used.

In other embodiments, the outer cover 52 of the primary absorbent member 40 and the topsheet 64 of the secondary absorbent member 60 may comprise a single web of material. In such embodiments, the web may substantially encircle the absorbent core 50 of the primary absorbent member 40 and extend outwardly therefrom to cover at least a portion of the secondary absorbent member 60. In these embodiments, the web may serve as a union means that connects the primary absorbent member 40 and the secondary absorbent member together. The compound sanitary napkin may also include additional union means to connect the primary absorbent member 40 to the secondary absorbent member. Suitable additional union means include but are not limited to adhesives, fusion bonds or any other union means as described herein.

The sanitary napkin 20 shown in FIGS. 1–3 preferably also comprises a pair of side extensions (or "side wrapping elements") 24 for folding around the side edges of the wearer's panties (or other undergarment). As shown in FIG. 1, the main body portion 22 is narrower in width measured across its central region 36 than at its end regions 32 and 34. The side wrapping elements 24 extend from at least the central region 36 of the main body portion 22. The side wrapping elements 24 are preferably configured so that the majority of the surface area of the side wrapping elements 24 is located laterally inward of the laterally outwardmost portion 42 of the main body portion 22. The sanitary napkin 20 can thus be thought of as having "internal flaps" that can fold around a wearer's undergarments.

The side wrapping elements 24 each have a proximal edge 74 and a distal edge 76. The side wrapping elements 24 are joined to the main body portion 22 at their proximal edges 74. In the embodiment shown in the drawings, the proximal edges 74 of the side wrapping elements 24 are preferably concave (relative to the distal edges 76). The distal edges 76 of the side wrapping elements 24 are preferably approximately parallel to the longitudinal centerline L. The sanitary napkin 20 may be thought of as having "internal flaps" because the side wrapping elements 24 are longitudinally inboard of the outermost edges of the lobes 38 of the main body portion 22 and the distal edges 76 of the side wrapping elements 24 preferably do not extend appreciably laterally outward beyond the outermost edges of the lobes 38 of the main body portion 22 of the sanitary napkin 20 and any peripheral flange around the same.

The side wrapping elements 24 of the embodiment shown in FIGS. 1–3 are preferably integral with the main body portion 22 of the sanitary napkin. In such a case, the topsheet 64 of the secondary absorbent member 60 may form a portion of the side wrapping elements 24 and the backsheet 66 may also form a portion thereof. For example, the topsheet 64 may form the body-facing surface of both the side wrapping elements 24 and the main body portion 22, and the backsheet 66 may form the garment-facing surface of the same. It is also possible for the absorbent material of the sanitary napkin 20 to extend into the side wrapping elements 24, as described in greater detail for the side flaps of the sanitary napkin in U.S. Pat. No. 4,917,697. In alternative embodiments, the side wrapping elements 24 may be comprised of separate pieces of material or elements which are attached to the main body portion 22. The side wrapping elements 24 may be joined in any of the manners that the side flaps are joined to the absorbent article described in U.S. Pat. No. 5,389,094 issued to Lavash, et al. on Feb. 14, 1995. When the side wrapping elements 24 comprise separate elements, they can be joined to the main body portion 22 by any techniques known to those skilled in the art. Such techniques include, but are not limited to adhesives, heat and/or pressure, ultrasonics, etc.

The side wrapping elements 24, whether they are integral with the main body portion or separate elements attached thereto, are each associated with main body portion 22 along a juncture. The juncture is typically a longitudinally-oriented (or "longitudinal") juncture, such as line of juncture 78. As used herein, the terms "juncture" (or "line of juncture") refer to regions where the side wrapping elements 24 extend from or are joined to the main body portion 22. The junctures 78 can be any of various curved or straight lines, but they are not limited to lines. Thus, the junctures can comprise regions, flanges, strips, intermittent lines, and the like. In the sanitary napkin 20 illustrated in FIG. 1, line of juncture 78 is a generally longitudinally oriented region that is concave relative to the distal edges 76 of the side wrapping elements. When the side wrapping elements 24 are integral with the main body portion 22, the lines of juncture 78 may represent lines of demarcation between the main body portion 22 and the side wrapping elements 24, although it is not necessary that there be a precise line of demarcation.

The side wrapping elements 24 are preferably more flexible (that is, less stiff) than those parts of the main body portion that form the longitudinal side edges 26 of the main body portion. The difference in stiffness along the longitudinal side edges 26 of the main body portion 22 provides the sanitary napkin 20 with a curved hinge line about which the side wrapping elements 24 may fold.

As shown in FIG. 1, each side wrapping element 24 is divided into a front half 80, and a back half 82 by a side wrapping element transverse centerline $T_1$. The side wrapping element transverse centerline $T_1$ may coincide with the principal transverse centerline T of the sanitary napkin, but this is not absolutely required. In other embodiments where the main body portion 22 is not symmetrical along its length, the side wrapping elements 24 may be located more toward one end of the main body portion, and the side wrapping element transverse centerline $T_1$ may, thus, be offset either to the front or to the rear of the principal transverse centerline T.

The side wrapping elements 24 are provided with weakened regions 84 that are more flexible than the adjacent regions 86 of the side wrapping elements. The weakened regions 84 are located so that on each side wrapping element 24, at least one weakened region, or portion thereof, lies on each side of the side wrapping element transverse centerline $T_1$. The weakened regions 84 are preferably at least partially disposed longitudinally away from the flap transverse centerline $T_1$ in both directions. (Thus, the weakened regions 84 may be described as being longitudinally "remote" from the side wrapping element transverse centerline $T_1$. In the most preferred case (as will be subsequently described in greater detail), the weakened regions 84 are located along a portion of the fold line where the side wrapping elements 24 are folded around the wearer's panty crotch. The fold line will typically be located along or adjacent the longitudinal juncture 78 of each side wrapping element 24. Since the terms "portions", "zones", and "regions", as used herein, refer to general areas, the weakened regions 84 are, thus, not limited to points which lie precisely on the line of juncture 78. Typically, they will include both those points which lie on the lines of juncture 78 as well as the surrounding areas of the sanitary napkin 20 which include the aforementioned fold lines). The longitudinal junctures, thus, may merely serve as approximations for the location of the weakened regions 84.

The weakened regions 84 are preferably also extensible. The weakened regions 84 may, thus, be thought of as comprising zones of differential extensibility (or "zones of extensibility"). The term "zones of differential extensibility", as used herein, refers to a portion of the side wrapping element 24 which is capable of extending a differing amount (preferably a greater amount), than adjacent regions 86 of the side wrapping element 24. The extensibility of the weakened regions 84 relieves the stresses which develop in the side wrapping elements 24 when they are folded around the sides of the wearer's panty crotch.

The weakened regions 84 are preferably primarily extensible generally outward in the transverse direction. As used herein, the phrase "generally in the transverse direction" means that the extensibility has a transverse component. All of the extension, however, need not be exactly parallel to the principal transverse centerline, T, of the sanitary napkin. For example, in the embodiment shown in FIG. 1, the weakened regions 84 are extensible in a direction between the longitudinal and transverse directions. The extensibility of the weakened regions 84, however, is preferably oriented more in the transverse direction than in the longitudinal direction so that it is still generally in the transverse direction. Although, it is also possible that in other embodiments, the extensibility of the weakened regions 84 can be oriented more in the longitudinal direction than the transverse direction, or even entirely in the longitudinal direction.

The weakened regions 84 can comprise any structure that is more flexible and extensible than the adjacent regions 86 of the side wrapping elements 24. Suitable structures for the weakened regions 84 include, but are not limited to zones of material that are mechanically strained, corrugated, "ring rolled" (the term "ring rolled" refers to a straining/activation achieved by feeding a material through intermeshing corrugated rolls), folded, formed into a Structural Elastic-Like Film (or "SELFed" structure) as described in U.S. Pat. No. 5,518,801 entitled "Web Materials Exhibiting Elastic-Like Behavior", issued to Chappell, et al. on May 21, 1996, and in U.S. patent application Ser. No. 08/124,180 filed by Mansfield, et al. (PCT Publication No. WO 94/10200), or pleated, or joined along a curved juncture. These weakened regions 84 (although shown in FIGS. 1–3 as only being part of the side wrapping elements 24), can comprise portions of the main body portion 22, portions of the side wrapping elements 24, or both. Examples of sanitary napkins having flaps and zones of differential extensibility are further described in U.S. Pat. No. 5,354,400 issued to Lavash, et al. on Oct. 11, 1994, and U.S. Pat. No. 5,389,094 issued to Lavash, et al. on Feb. 14, 1995. Other, but less preferred, examples of structures that can provide the side wrapping elements 24 with a degree of flexibility and extensibility are the notches shown in FIG. 5 of U.S. Pat. No. B1 4,589,876 issued to Van Tilburg and the stress relief means described in U.S. Pat. No. 4,917,697 issued to Osborn, et al.

The sanitary napkin 20 shown in FIGS. 1–3 has side wrapping elements 24 that have been provided with weakened regions 84 by ring rolling the desired regions of the side wrapping elements 24. The weakened regions 84 are ring rolled in accordance with methods described in U.S. Pat. No. 4,107,364 issued to Sisson on Aug. 15, 1978, U.S. Pat. No. 4,834,741 issued to Sabee on May 30, 1989, U.S. Pat. No. 5,143,679 issued to Gerald M. Weber, et al. on Sep. 1, 1992, U.S. Pat. No. 5,156,793 issued to Kenneth B. Buell, et al. on Oct. 20, 1992, and U.S. Pat. No. 5,167,897 issued to Gerald M. Weber, et al. on Dec. 1, 1992. The ring rolling (also known as "pre-corrugating") forms corrugations in the weakened regions 84. The corrugations comprise ridges and valleys that are defined by fold lines 88. The fold lines 88 may form any angle desired relative to the principal longitudinal centerline L. In the preferred embodiment shown in FIGS. 1–3, the fold lines 88 form an angle of between about 40°–45° with the principal longitudinal centerline L. This will provide the desired direction of extensibility.

The side wrapping elements 24 are sufficiently flexible and are sized and configured so that they are capable of folding around the side edges of a crotch region of a wearer's undergarment. In order to be capable of folding around the sides of an undergarment, the side wrapping elements 24 must be of a certain minimum size (that is, length and width). Otherwise, the adjacent stiffer portions of the sanitary napkin 20, such as the lobes 38, of the main body portion 22, to which the side wrapping elements 24 are joined, will restrict and prevent the side wrapping elements 24 from folding. The side wrapping elements 24 preferably range in size from about 2 cm in width (transverse direction from their proximal edge to their distal edge) and about 16.5 cm in length (longitudinal direction) up to about 4.5 or 5 cm in width and about 23.5 cm in length. The side wrapping elements 24 in the embodiment shown in FIGS. 1–3 are preferably about 2 inches (about 5 cm) in width from their proximal edge to their distal edge, and about 8 inches (about 20 cm) in length, and measure greater than or equal to about 160 mm, more preferably greater than or equal to about 170 mm, more preferably greater than or equal to about 180 mm, more preferably still greater than or equal to about 190 mm, and most preferably greater than or equal to about 200 mm along their curvilinear proximal edge.

The enhanced flexibility and extensibility of the weakened regions 84, along with the difference in flexibility between the side wrapping elements 24 and longitudinal side edges 26 of the main body portion 22, allows the side wrapping elements 24 to fold smoothly around the edges of the wearer's panties. If the longitudinal side edges 26 of the main body portion 22 are approximately the same size and shape as the side edges of the wearer's panties, the side wrapping elements 24, in a most preferred embodiment, can fold on a curvilinear line virtually exactly along the side edges of the wearer's panties. Preferably, the side wrapping elements 24 fold at least along a generally curvilinear line that lies at least generally along the side edges of the wearer's panties. The side wrapping elements 24 can, if desired, bend through an angle of 180 degrees, and be attached to the underside of the wearer's panties. The fact that the side wrapping elements 24 can fold along a curvilinear line, allows the side wrapping elements to form a flat fold along the length of the edges of the wearer's panties. This reduces the tendency for the side wrapping elements to bunch longitudinally inward which would reduce the area of the wearer's panties the side wrapping elements 24 are able to cover. It also reduces the tendency for the ends of the main body portion along the longitudinal side edges thereof to become detached from the wearer's panties and lift up and fold over onto the topsheet. It further substantially reduces, if not eliminates, any tendency for the side wrapping elements 24 to become unattached to the underside of the wearer's panties (or for the fastener on the side wrapping elements to "pop" off from their attachment with the underside of the panties).

The sanitary napkin 20 preferably also has fasteners that are adapted to secure the sanitary napkin 20 to the crotch region of an undergarment. FIGS. 2 and 3 show one preferred type of fastener, in the form of an adhesive attachment means, such as central pad adhesive 94 and side wrapping element adhesive 96. The fasteners used with the sanitary napkin of the present invention are, however, not limited to adhesive attachment means. Any type of fastener used in the art can be used for such purpose. For example, the sanitary napkin 20 could be secured to the wearer's undergarment by frictional fasteners, mechanical fasteners, or a combination of any of the foregoing types of fasteners. For simplicity, however, the fasteners will be described in terms of adhesive attachment means and are preferably pressure sensitive adhesive fasteners. Suitable pressure sensitive adhesive fasteners are described in greater detail in U.S. Pat. No. 4,917,697.

The adhesive fasteners 94 and 96 can be arranged in any suitable configuration. FIG. 3 shows one possible panty fastener pattern. The panty fastener pattern shown in FIG. 3 comprises a pair of longitudinally-oriented central pad fasteners 94 that lie on opposite sides of the principal longitudinal centerline L. The longitudinally-oriented central pad fasteners 94 shown in FIG. 3 preferably extend substantially the entire length of the absorbent element 62 of the secondary absorbent member 60. The longitudinally-oriented central pad fasteners 94 preferably each have an inside edge 94A which is generally linear. The inside edges 94A of the longitudinally-oriented fasteners 94 are preferably spaced away from each other and from the principal longitudinal centerline L of the sanitary napkin 20. This allows a longitudinally-oriented central region of the sanitary napkin 20 (that does not have a fastener thereon) to move apart from the wearer's panties and move into close contact with the wearer's body. The longitudinally-oriented central pad fasteners 94 preferably have outside edges 94B and ends 94C that are shaped similarly to the outer edges of the absorbent element 62 of the secondary absorbent member 60. This provides a central pad fastener 94 that is generally hourglass shaped with a longitudinally oriented gap in the center. In addition to the longitudinally oriented central pad fasteners 94, the sanitary napkin 20 preferably has a rectangular side wrapping element fastener 96 on each side wrapping element 24 which lies along the transverse centerline T of the sanitary napkin 20. It is to be understood that this is only one possible fastener configuration, and that many other configurations are possible.

The adhesive attachment means, such as the central pad adhesive 94 and the side wrapping element adhesive fasteners 96, may each be covered by separate removable release liners to keep the adhesives from sticking to extraneous surfaces prior to use. A suitable release liner that can be used for the side wrapping element fasteners 96 is described in U.S. patent application Ser. No. 08/247,912 filed May 23, 1994, entitled "Absorbent Article Having Flaps With Unitary Release Strip" in the name of Osborn, which was originally filed Jun. 5, 1990 (PCT Publication No. WO 91/18574, published Dec. 12, 1991).

Figure 4:
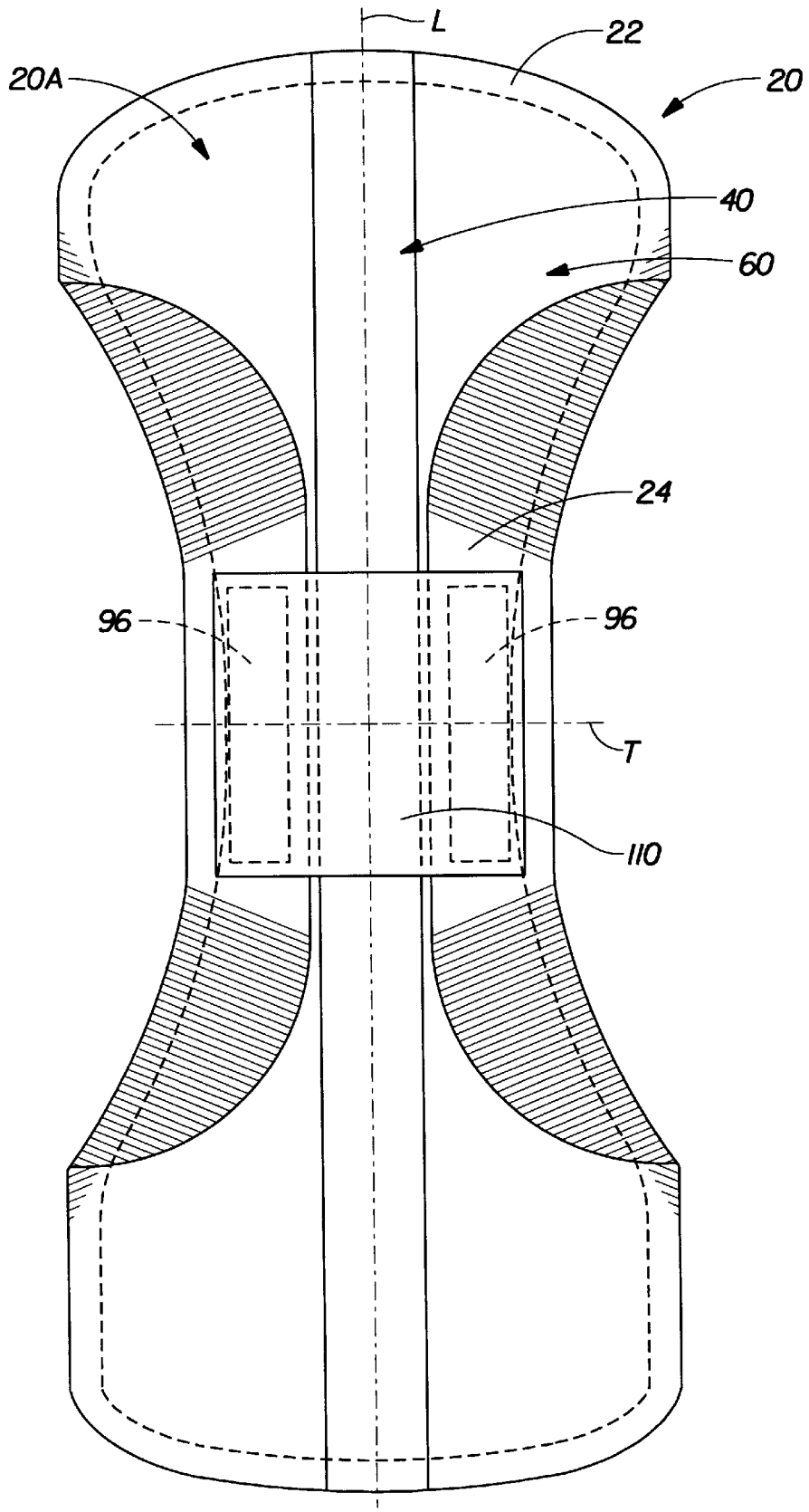
FIG. 4 is a top plan view of the sanitary napkin of the present invention shown with the side wrapping elements folded over the body-facing side of the main body portion, and the fasteners thereon covered with a unitary release strip.
Figure 5:
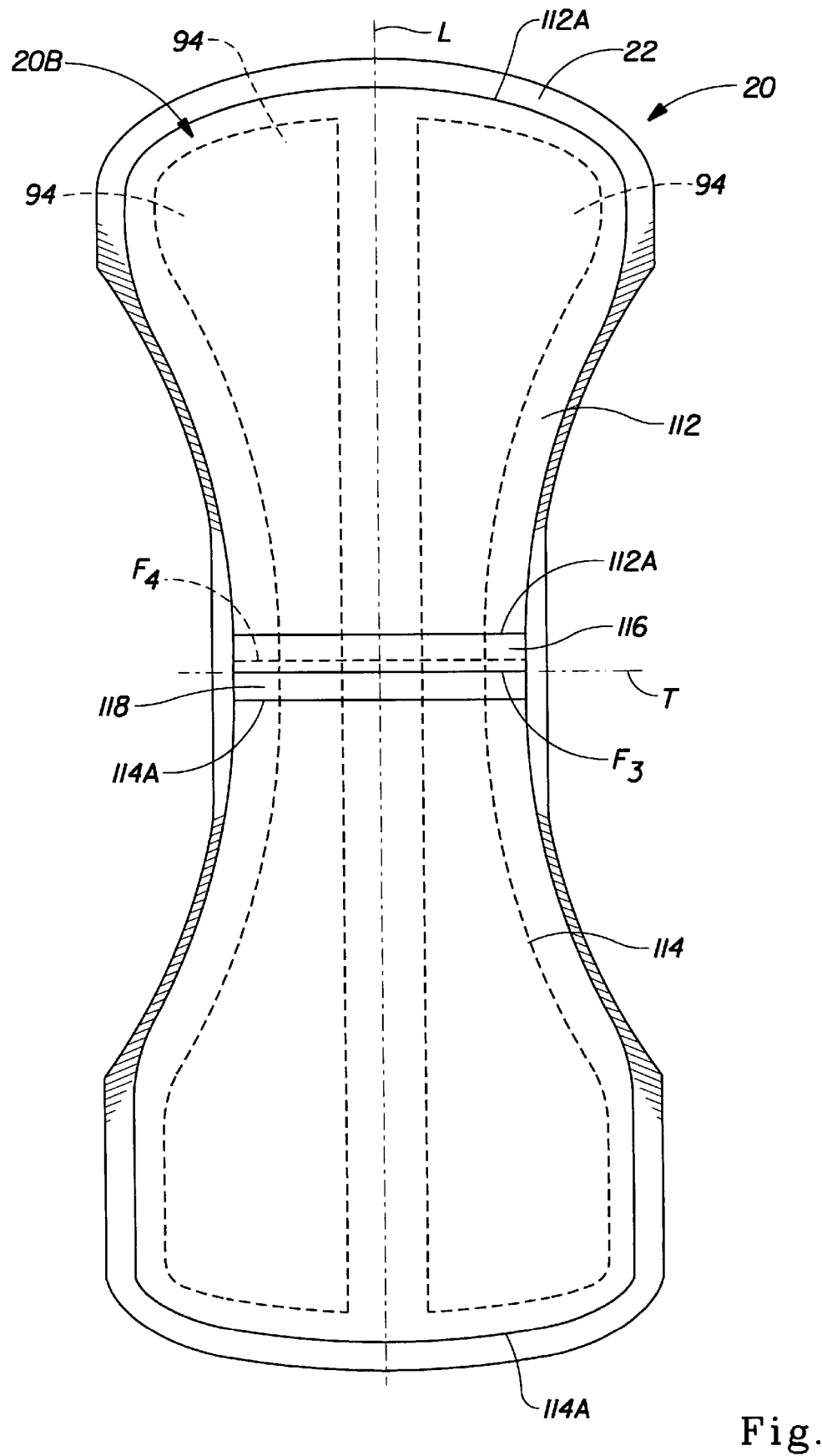
FIG. 5 is a bottom plan view of the sanitary napkin shown in FIG. 4 which is provided with a multiple piece panty fastener cover.

FIGS. 4 and 5 show one way of covering the adhesive fasteners on the garment facing side of the sanitary napkin. As FIG. 4 shows, in this embodiment, the side wrapping elements 24 are folded over the body-facing side 20A of the main body portion 22 and the adhesive fasteners 96 thereon are covered with a unitary release strip 110. As shown in FIG. 11, the adhesive fasteners 94 on the garment-facing side 20B of the main body portion 22 are covered with multiple release papers such as release papers 112 and 114. In the embodiment shown in FIG. 5, these multiple release papers 112 and 114 are oriented in an end-to-end relationship in the longitudinal direction. Each of the release papers 112 and 114 generally resembles the shape of half of an hourglass. The release papers 112 and 114 may have a portion adjacent at least one edge, such as at an end edge, 112A) that is nonadhesive, that overlaps with a portion adjacent the end edge (such as 114A) of the adjacent release paper. In the preferred embodiment shown, the non-adhesive end edge is also folded back (such as along $F_3$ and $F_4$) to provide a graspable tab 116 and 118 for the consumer to hold in order to more easily remove the release papers 112 and 114.

In other embodiments, the end edges of the release papers may abut, rather than overlap. In still other embodiments, the end edges may be spaced slightly apart. Numerous other embodiments of multiple release paper arrangements are also possible. For example, in other embodiments, the multiple release papers may be arranged in a side-by-side arrangement, rather than end to end. The multiple release paper embodiments described above are particularly useful when the main body portion 22 of the sanitary napkin is extensible, highly flexible, or both. Such multiple release paper arrangements provide ease in handling these types of sanitary napkins and allow the wearer to place the same in her panties without portions of the adhesive fastener on the sanitary napkin folding over and inadvertently sticking to other portions of the sanitary napkin.

In other embodiments, the central pad adhesive 94 is covered by an arrangement where the release liner comprises a releasable wrapper 100 that also serves as an individual package for the sanitary napkin. Suitable release liners that serve as an individual package for a sanitary napkin are described generally in U.S. Pat. No. 4,556,146 issued to Swanson, et al. (which discloses a tri-folded sanitary napkin and wrapper). Other features that such a package can be provided with are described in U.S. Pat. No. 5,181,610 issued to Quick, U.S. Pat. No. 5,413,568 issued to Roach, et al., U.S. Pat. No. 5,462,166 issued to Minton, et al., and U.S. Pat. No. 5,484,636 issued to Berg, Jr., et al.

Figure 6:
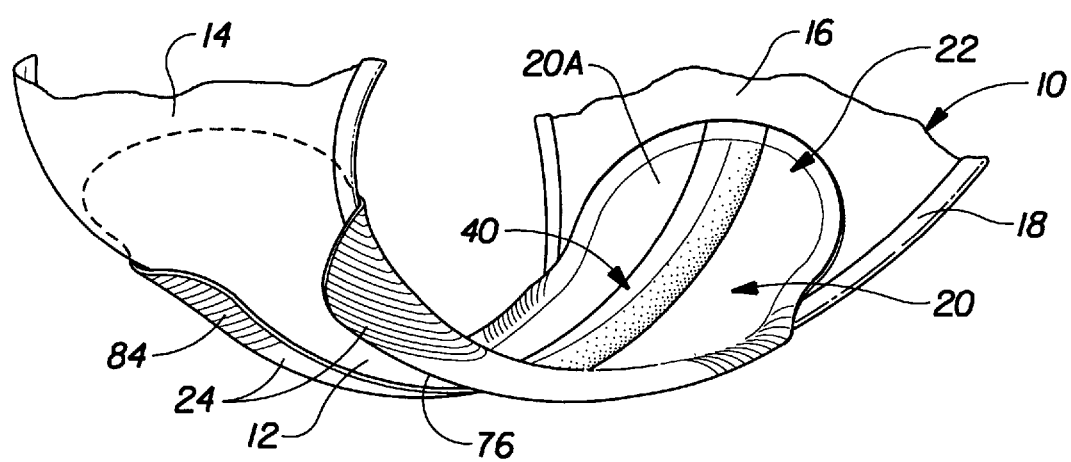
FIG. 6 is a perspective view of the sanitary napkin in a wearer's panties.

FIG. 6 is a depiction of the sanitary napkin 20 of the present invention in place in an undergarment of the type commonly worn by many women and well known as a panty 10. The configuration of the sanitary napkin 20 in the panty shown in FIG. 6 is presented primarily for purposes of discussion, rather than to limit the possible configurations the sanitary napkin may take in use. It should be understood that the sanitary napkin 20 described herein may also take other configurations in use. For example, the side wrapping elements of the sanitary napkin 20 can, if desired, take in-use configurations similar to those of the flaps described in U.S. Pat. Nos. 4,687,478 and 5,267,992 issued to Van Tilburg or U.S. Pat. No. 5,354,400 issued to Lavash, et al. Of course, the in-use configuration will differ somewhat since the span of the side wrapping elements 24 will typically be less than such flaps.

The panty 10 comprises a crotch portion 12, a front section 14, and a back section 16. The crotch portion 12 joins the front and back sections and comprises two elasticized side edges 18. As shown in FIG. 6, the center of main body portion 22 is placed in the crotch portion 12 of the panty 10 with the garment-facing side of the main body portion in contact with the inner surface of crotch portion 12 of the panty and one end of main body portion 22 extending towards the front section 14 of the panty and the other end towards the back section 16. Central pad adhesive 94 maintains main body portion 22 in position. The distal portions 76 of side wrapping elements 24 are folded around the elasticized side edges 18 of the panty. The flap adhesive portions 96 secure the side wrapping elements 24 to the underside of the panty.

Numerous other alternative embodiments of the absorbent article and wrappers described herein are possible.

Figure 7:
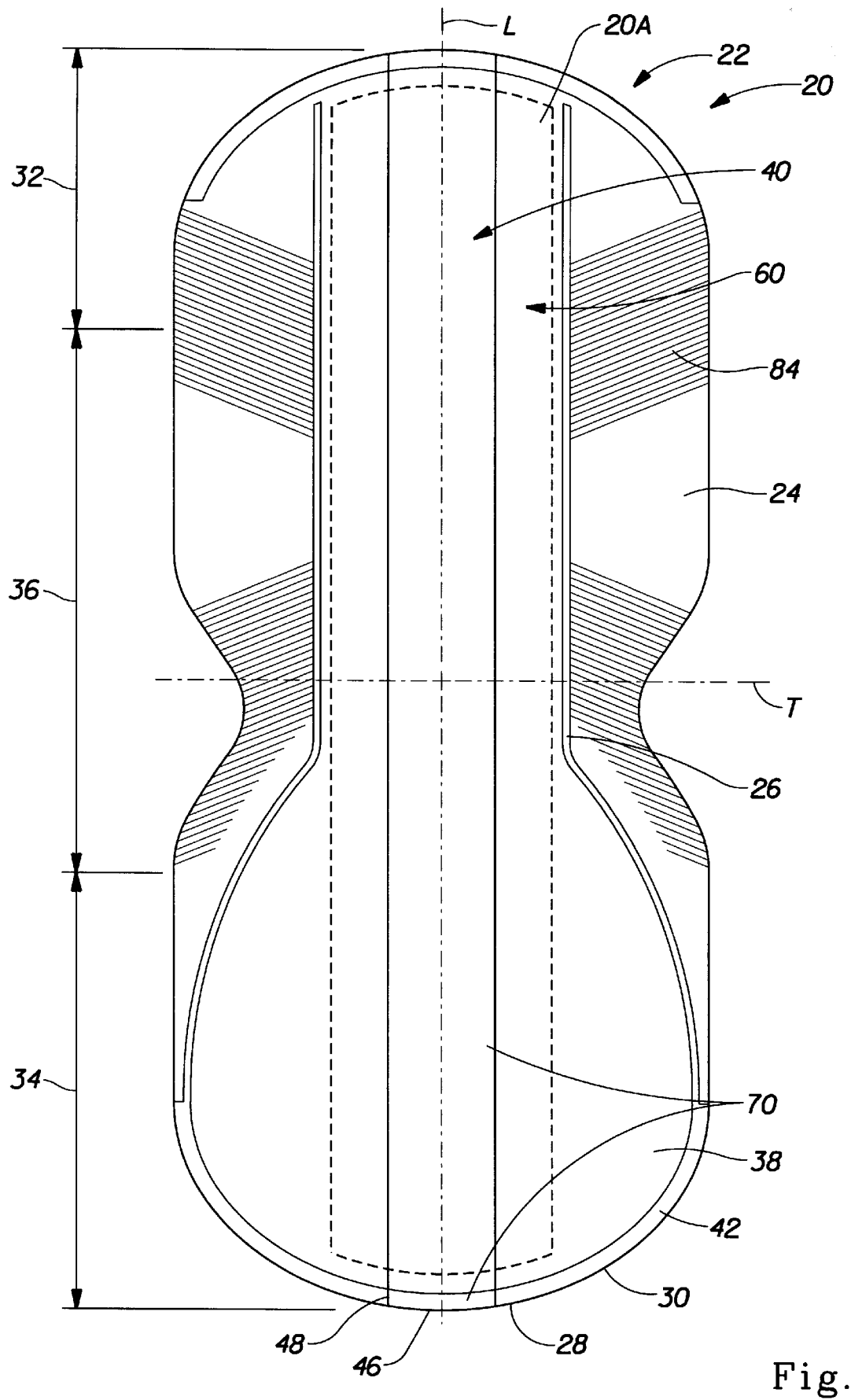
FIG. 7 is a top plan view of another embodiment of a sanitary napkin.

FIG. 7 shows an alternative embodiment of the sanitary napkin which is adapted for use in Japanese menstrual shorts. The embodiment shown in FIG. 9 has a different plan view shape than the embodiment shown in the preceding drawing figures. Most noticeably, the sanitary napkin 20 in FIG. 7 only has lobes 38 in the rear and region 34 of the sanitary napkin 20. The longitudinal side edges of the main body portion 22 are generally linear in the front end region 32. In addition, the zones of differential extensibility 84, particularly those closest to the rear end region 34, are shifted forward relative to their position in the embodiment shown in the preceding drawing figures so that these zones of differential extensibility 84 are nearly centered about the transverse centerline T of the sanitary napkin 20.

In the embodiment shown in FIG. 7, the primary absorbent member 40 is slightly wider and shorter in height than the absorbent member on the embodiment shown in the preceding drawing figures. The absorbent core 50 of such an embodiment may comprise two strips of foam, one of which serves as the acquisition/fit portion, and one of which serves as the storage portion. Each of these strips may have the same width (e.g., approximately 1.4 inches (about 3.5 cm)), and the strips may each be approximately 2 to 3 mm in height. Additional strips, of course, can be added as either acquisition/fit portions or storage portions. The total height of the primary absorbent member 40 may, therefore, be in the range of between about 6 and about 8 mm. The various layers of the absorbent core 50 can all be of the same length, or they can decrease in length from bottom to top. For example, in one variation of such an embodiment, the primary absorbent member 40 can be only a portion of the length of the secondary absorbent member 60, and be shifted so that it lies almost entirely in the central region 36 and rear end region 34.

In other embodiments, the characteristics of the foam used in the absorbent core can be varied. For example, the foams used in the present invention typically have a homogeneous structure, i.e., each portion of the absorbent core 50 is relatively uniform in terms of cell and hole sizes. However, if desired, these foams can be prepared so as to have a heterogeneous structure. For example, the foams can have regions of lower and higher capillary specific surface area and/or decreasing average cell size from their top (or portion closest to the wearer) to their bottom to provide a capillary gradient. The foams can have two ("bi-modal") or more cell sizes. The capillary gradient can be continuous or stepped between the different regions of the absorbent core. Such gradients can be achieved by varying the process conditions used in making the foam as described in the Example provided previously. Alternatively, the different foams could be formed side-by-side, and the portion of the foam with a lower capillarity can be folded over a portion of the foam with higher capillarity. Numerous other folded and pleated embodiments are possible. the portions of the foam can be folded over each other to create a vertically stacked arrangement, an arrangement where the folded or pleated layers are side-by-side, or more complicated arrangements where the folded portions are at an angle with the other portions of the foam.

In another example, the foam can have regions of high and low capillary specific surface area, such as along the length versus the width of the foam. This provides the ability to control the direction of movement of the absorbed fluid within the foam and is particularly advantageous when the foam has a rectangular configuration. By providing a heterogeneous structure, the absorbed liquids can be induced to move along the length of the foam, as opposed to its width, thereby minimizing potential leakage along the sides of the catamenial product that can occur more readily if the foam has a homogeneous structure. The regions of high and low capillary specific surface area described above can be obtained by using multiple mixing heads, such as is described in U.S. patent application Ser. No. 08/612,643 (P&G Case 5985) entitled "Heterogeneous Foam Materials", filed on Mar. 8, 1996 in the name of Shiveley, et al., or by "pulsed" conditions during the making or pouring of the HIPE, such as changes in mixer speed and/or by adjusting the water to oil phase ratio.

In other alternative embodiments, the storage portion 56 may comprise absorbent gelling materials. The absorbent gelling materials may be provided in numerous possible forms. For example, the absorbent gelling materials may be provided in the form of a layer of particles of absorbent gelling material, in the form of a web of material containing absorbent gelling material, or in the form of a laminate comprising particles of absorbent gelling material.

It may be desirable to provide a compound sanitary napkin having a primary absorbent member with varying degrees of width or caliper throughout its length. For example, the primary absorbent member may be relatively thicker in the central region 36 as opposed to the end regions 32 and 34. Alternatively, the primary absorbent member may be relatively thinner in the central region 36 as opposed to the end regions 32 and 34. In alternative embodiments, the primary absorbent component 40 could be shifted longitudinally forward or backward relative to the transverse centerline T.

In other alternative embodiments, the sanitary napkin 20 need not be in the form of a compound sanitary napkin. For example, a sanitary napkin can be provided in the configuration of any of those sanitary napkins described in allowed U.S. patent application Ser. No. 08/563,879, filed Nov. 21, 1995 (PCT International Publication No. WO 94/16658, entitled "Generally Thin, Flexible Sanitary Napkin With Central Absorbent Hump", published in the name of Osborn, et al. on Aug. 4, 1994), where the hump comprises the foam described herein. In other alternative embodiments, the sanitary napkin can be provided in the configuration of the sanitary napkin described in U.S. patent application Ser. No. 08/531,533, entitled "Absorbent Article With Clean Appearance and Capacity Signal Means" filed Sep. 21, 1995, in the name of Hammons, et al. (P&G Case 5823) with the foam described herein in the center region of the sanitary napkin.

In other alternative embodiments, rather than having the side wrapping elements 24 described herein, the sanitary napkin 20 may have flaps which extend laterally from the side edges of the main body portion 22. Pat.s describing flaps suitable or adaptable for use with the secondary absorbent member 60 of the compound sanitary napkin 20 of the present invention include U.S. Pat. No. 4,687,478 issued to Van Tilburg on Aug. 18, 1987; U.S. Pat. No. 4,589,876 issued to Van Tilburg on May 20, 1986; U.S. Pat. No. 4,608,047 issued to Mattingly on Aug. 26, 1986; and U.S. Pat. No. 5,389,094 issued to Lavash, et al. on Feb. 14, 1995.

Optionally, the secondary absorbent member may comprise components that naturally wrap the sides of a wearer's panties. A sanitary napkin having components that naturally wrap the sides of a wearer's panties suitable for use with the secondary absorbent member of the compound sanitary napkin 20 of the present invention are disclosed in U.S.

patent application Ser. No. 08/096,121, (P&G Case 4961) entitled "Absorbent Article having Panty Covering Components that Naturally Wrap the Sides of Panties", filed Jul. 22, 1993, in the names of Lavash, et al and U.S. patent application Ser. No. 08/277,733 (P&G Case 5354) entitled "Absorbent Articles Having Undergarment Covering Components with Zones of Extensibility", filed Jul. 20, 1994, in the names of Weinberger, et al.

The individual components of the primary absorbent member 40 and the secondary absorbent member 60 may be comprised of components that are extensible (preferably, capable of stretching) particularly in the longitudinal direction when the compound sanitary napkin is worn. Preferably, the compound sanitary napkin is capable of elongating in the longitudinal direction between about 15% and about 40% of its unstretched length. This extensibility provide better in-use fit, comfort, and decreased staining when the compound sanitary napkin is affixed to the wearer's undergarments. Sanitary napkins having extensible components are described in U.S. patent application Ser. Nos. 07/915,133 and 07/915,284 both filed Jul. 23, 1992, in the name of Osborn, et al. (PCT Publication Nos. WO 93/01785 and 93/01786, both published Feb. 4, 1993).

In addition, the features of the present invention could be provided on other types of absorbent articles, For example, suitable absorbent articles in the form of pantiliners that could be provided with the features of the present invention are disclosed in U.S. Pat. No. 4,738,676 entitled "Pantiliner" issued to Osborn on Apr. 19, 1988. Suitable absorbent articles, at least some of which are in the form of adult incontinence products that could be provided with the features of the present invention, are described in U.S. Pat. Nos. 5,300,054 issued to Feist, et al. on Apr. 5, 1994, and 5,304,161 issued to Noel, et al. on Apr. 19, 1994.

TEST METHODS

In describing the present invention, a number of characteristics of the HIPE foam absorbent structures are set forth. Where reported, these characteristics can be determined using the following test fluids and test methods.

I) Test Fluids and Foam Sample Preparation
A) Test Fluid-Synthetic Urine

Several of the measurements described in the tests herein involve the use of a test fluid such as synthetic urine, ethanol, or 2-propanol (isopropyl alcohol). The synthetic urine utilized in a number of the tests described hereafter is made from a commercially available synthetic urine preparation manufactured by Jayco Pharmaceuticals (Mechanicsburg, Pa., 17055). This Jayco synthetic urine made from the preparation comprises KCl, 0.2%; $Na_2SO_4$, 0.2%; $NH_4H_2PO_4$, 0.085%; $(NH_4)_2HPO_4$, 0.015%; $CaCl_2*2H_2O$, 0.025%; and $MgCl_2*6H_2O$, 0.05%. (weight %'s) The synthetic urine samples are prepared according to the label instructions using distilled water. To aid dissolution, the Jayco salt mixture is slowly added to the water. The sample is filtered if necessary to remove any particulates. Any unused synthetic urine is discarded after one week. To improve visibility of the fluid, 5 drops of blue food color can be added per liter of synthetic urine solution. The Jayco synthetic urine utilized has a surface tension of 65±5 dynes/cm.

B) Foam Sample Preparation

A number of the following tests involve the preparation and testing of foam samples of a particular specified size. Unless otherwise specified, foam samples of the requisite size should be cut from larger blocks of foam using a sharp reciprocating knife saw. Use of this or equivalent type of foam cutting device serves to substantially eliminate sample edge flaws which could have an adverse impact on certain of the measurements made in carrying out the several test procedures hereafter set forth.

Sample size specification will also generally include a dimension for sample caliper or thickness. Caliper or thickness measurements for purpose of the present invention should be made when the foam sample is under a confining pressure of 0.05 psi (350 Pa). All measurements of foam density and dry weight are usually carried out after the foam sample has been wager washed and dried, as described hereafter.

II) Determination of Properties, Features or Characteristics of Foam
A) Collapsed State 1) Expansion Pressure This test directly measures the stored energy in the collapsed foam. The stored energy of the collapsed foam is released when it is flooded with an amount of water greater than its free absorbent capacity. Expansion pressure is measured while the fully wetted foam is being held by compressive forces at its collapsed caliper (thickness).

To conduct this test, a 23.8 mm. diameter cylinder of the collapsed foam is carefully cut out using a punch. The caliper of this cut sample is measured with a strain gauge (e.g., Ono-Sokki Model EG-225) to the nearest 0.005 mm. In performing the stress relaxation test, a Rheometrics Model RSA II is used having a parallel plate assembly capable of retaining liquid. This parallel plate assembly comprises a bottom cup plate having a cylindrical chamber with an inside diameter of 29 mm., and a top plate having a circular member with a diameter of 25 mm.

The cut, dry sample is placed within the chamber of the bottom cup plate and centered under the circular member of the top plate. The entire assembly/sample is then equilibrated at 88° F. (31. 1° C.) for at least 10 minutes, with the top plate being adjusted to rest on the cut sample with a force of about 10 g. The Rheometrics Model RSA II is programmed to run a stress-relaxation test at 0.5% strain (in compression) at 88° F. (31.1° C.). While monitoring stress as a function of time, enough water having a temperature of 88° F. (31 .1° C.) is quickly added to the bottom cup plate using a syringe to insure complete saturation of the cut sample (e.g., 3 mL in 1 second). The pressure the cut sample exerts on the plates as it tries to expand (i.e., its expansion pressure) is recorded for at least 15 minutes after the point at which the water is added; the value at 5 minutes if recorded as the expansion pressure of the cut sample.

Resistance to Compression Deflection

Resistance to compression deflection can be quantified for purposes of this invention by measuring the amount of strain (% caliper reduction) produced in a foam sample, which has been saturated and fully expanded with synthetic urine, after stress in the form of a 0.74 psi (5.1 kPa) confining pressure has been applied to the sample.

The foam samples, Jayco synthetic urine and equipment used to make measurements are all equilibrated to a temperature of 88° F. (31.1° C.). Measurements are also performed at this temperature.

A foam sample sheet in its collapsed state is saturated to its free absorbent capacity with Jayco synthetic urine. After 2 minutes, a cylinder having a 1 $in^2$ (6.5 $cm^2$) circular surface area is punched out of the saturated, fully expanded sheet. A dial-type gauge suitable for making caliper measurements is positioned on the sample. Any gauge fitted with a foot having a circular surface area of at least 1 $in^2$ (6.5 $cm^2$)

and capable of measuring caliper dimensions to 0.001 in (0.025 mm) can be employed. Examples of such gauges are an Ames model 482 (Ames Co.; Waltham, Mass.) or an Ono-Sokki model EG-225 (Ono-Sokki Co., Ltd.; Japan).

A force is then applied to the foot so that the saturated foam sample on the screen is subjected to a confining pressure of 0.74 psi (5.1 kPa) for 15 minutes. At the end of this time, the dial gauge is used to measure the change in sample caliper which occurs as a consequence of the application of the confining pressure. From the initial and final caliper measurements, a percent strain induced can be calculated for the sample.

Capillary Suction Specific Surface Area

Capillary suction specific surface area of the foam can be determined from the equilibrium weight uptake of a test liquid of known low surface tension. In this instance, absolute ethanol (flash point is 10° C.) is used.

To conduct the test, a tared foam sample strip of suitable dimensions (e.g., >35 cm long×2 cm wide×0.25 cm thick) is equilibrated at 22°±2° C., is positioned vertically and at one end is immersed 1–2 mm into a reservoir of the ethanol using a lab jack. The ethanol is allowed to wick up the foam strip to its equilibrium height which should be less than the sample length. The ethanol containing strip is then weighed to determine the weight of total ethanol uptake. During this procedure the sample should be shielded, for example with a capped glass cylinder, to prevent ethanol evaporation. The ethanol is then allowed to evaporate from the foam sample which is then water washed, dried and weighed.

Specific surface area of the foam sample can be calculated from the following formula:

$$S_c = \frac{M_e G L_n}{M_{n\gamma_e}}$$

where $S_c$=capillary suction specific surface area in cm$^2$/gm; $M_e$=mass of liquid uptake of ethanol in gms; G=the gravitational constant which is 980 cm/sec$^2$; $L_n$=total length of wet sample in cm; $M_n$=mass of dry sample in gm; and $\gamma_e$=surface tension of ethanol which is 22.3 dynes/cm. Values obtained can then be divided by 10000 cm$^2$/m$^2$ to provide capillary suction specific surface area in m$^2$/g.

1) Free Absorbent Capacity

In this test, a foam sample is saturated at 88° F. (31.1° C.) with Jayco synthetic urine. Dry foam samples are cut into 1 in$^2$ (6.5 cm$^2$) circular surface area ×0.1 inch (0.25 cm) thick cylinders or the equivalent. Such cylindrical samples can be prepared by using a sharp punch 1.13 inches (2.87 cm) in diameter on a 0.1 inch (0.25 cm) sheet of foam. The dry foam samples (after water washing and drying) are each weighed to determine a dry weight (DW). Three of such samples are weighed to determine an average dry weight (DW). The Measured Free Capacity (MFC) of these samples is then determined by the following steps:

a) The foam samples are immersed in the 2-propanol in a crystallizing dish and allowed to saturate. At this point the sample may be squeezed a few times to expel air.

b) Each sample is removed without squeezing 2-propanol out of it. Excess fluid is allowed to drip off of the sample in the flat position for about 30 seconds. Each sample is then weighed wet to determine a wet weight (WW).

c) Steps a) and b) are repeated two more times and an average wet weight (WW) is calculated.

Measured Free Capacity (MFC, g/g) is the weight of 2-propanol in the saturated Foam per unit mass of dry foam. MFC is calculated according to the formula.

$$MFC = \frac{[WW(g) - DW(g)]}{DW(g)}$$

Available pore volume is then calculated by dividing the MFC of the foam for 2-propanol by the density of 2-propanol which is 0.785 g/mL. This gives an available pore volume for the foam in mL/g.

2) Vertical Wicking Rate and Vertical Wicking Absorbent Capacity

Vertical wicking rate and vertical wicking absorbent capacity are measures of the ability of a dry foam to wick fluid vertically from a reservoir. The time required for the fluid front to wick through a 5 cm vertical length of a strip of foam is measured to give a vertical wicking rate. After fluid wicks to its equilibrium height, the amount of fluid held by the foam strip at a particular vertical wicking height (e.g., 4.5 inches or 11.4 cm) is determined to give a vertical wicking absorbent capacity.

Jayco synthetic urine colored with blue food coloring is used in the following methods to determine vertical wicking rate and vertical wicking absorbent capacity. In this test procedure, the materials are equilibrated at 37° C. and the test is performed at the same temperature.

A strip of foam approximately 70 cm long×2 cm wide× 0.25 cm thick is supported vertically with one end immersed 1 to 2 mm into a reservoir of synthetic urine. The liquid is allowed to wick up the foam strip to its equilibrium height (e.g., about 18 hours), which should be less than the sample length. During this procedure, the sample should be shielded, for example with a capped glass cylinder, to prevent evaporation.

The time needed to wick 5 cm is used as a measure of vertical wicking rate. The equilibrium wet weight can be recorded and used to calculate Adhesion Tension, as described below.

The sample is quickly removed and placed on a non-absorbent surface where it is cut into 1 inch (2.54 cm) pieces using a tool sharp enough not to compress the foam sample. Each piece is weighed, washed with water, dried and then reweighed. The absorbent capacity is calculated for each piece. The absorbent capacity of the 1 inch segment centered at 4.5 inches (11.4 cm) wicking height is the parameter most desirably determined.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention.

What is claimed is:

1. An absorbent article for wearing by a human female, said absorbent article comprising:

a primary absorbent component having a base, an apex, said base and apex each having a width, wherein the width of said base is greater than the width of said apex and the width of said primary absorbent component decreases from said base to said apex, and at least a portion of said primary absorbent component has a width of less than or equal to about 9.5 mm, said primary absorbent component comprises a compressible, hydrophilic, flexible, nonionic polymeric foam structure of interconnected open cells which is capable of absorbing blood and blood-based liquids, wherein said foam structure is resiliently compressible and has a resistance to compression deflection of from about 5% to about 85% when measured under a confining pressure of 0.74 psi at 31 degrees C. after 15 minutes, according to the Resistance to Compression Deflection Test.

2. The absorbent article of claim 1 wherein at least a portion of said foam structure adjacent said apex has a resistance to compression deflection of from about 40% to about 85% under such conditions.

3. The absorbent article of claim 2 wherein at least a portion of said foam structure adjacent said apex has a resistance to compression deflection of from about 60% to about 85% under such conditions.

4. The absorbent article of claim 1 wherein said foam structure is compressible under such forces that when it is placed in the space between the wearer's labia majora, it will be compressed without deforming the wearer's labia, and will be molded by the wearer's labia and conform to the shape thereof.

5. The absorbent article of claim 1 wherein said primary absorbent component has a length and a height measured along at least a portion of said length which is between about 5 mm and about 30 mm so that at least a portion of said primary absorbent component will fit in the wearer's gluteal groove.

6. The absorbent article of claim 1 wherein said foam structure has:
A) a capillary specific surface area in the range of from about 0.0080 to about 0.49 $m^2/cc$;
B) a free absorbent capacity of from about 20 to bout 125 g/g; and
C) inorganic salt content of less than about 2% by dry weight of foam.

7. The absorbent article of claim 1 wherein said foam structure has a Tg of less than about 50° C.

8. The absorbent article of claim 1 wherein said foam structure has a cell size of from about 30 to about 130 $\mu$m.

9. The absorbent article of claim 1 wherein said foam structure has a hole size of from about 5 to about 30 $\mu$m.

10. The absorbent article of claim 1 wherein said foam structure has the ability to wick artificial menstrual fluid vertically to a height of 5 cm in less than about 40 minutes.

11. The absorbent article of claim 1 wherein said foam structure comprises a single homogeneous foam structure.

12. The absorbent article of claim 1 wherein said foam structure comprises a heterogeneous mixture of a first foam portion having a capillary specific surface area of from about 0.012 to about 0.020 $m^2/cc$ and a second foam portion having a capillary specific surface area of from about 0.020 to about 0.026 $m^2/cc$.

13. An absorbent article for wearing by a human female, said absorbent article comprising:
a primary absorbent component having a base, an apex, said base and apex each having a width, wherein the width of said base is greater than the width of said apex and the width of said primary absorbent component decreases from said base to said apex, and at least a portion of said primary absorbent component has a width of less than or equal to about 9.5 mm, said primary absorbent component comprises a compressible, hydrophilic, flexible, nonionic polymeric foam structure of interconnected open cells which is capable of absorbing blood and blood-based liquids, wherein said foam structure is resiliently compressible and has a resistance to compression deflection of from about 40% to about 85% when measured under a confining pressure of 0.74 psi at 31 degrees C. after 15 minutes, according to the Resistance to Compression Deflection Test, and said primary absorbent component is capable of at least partially fitting in the space between the wearer's labia.

14. The absorbent article of claim 13 wherein said acquisition/fit component has an average cell diameter of between about 100–130 microns and said storage component has an average cell diameter of between about 35–60 microns.

15. An absorbent article for wearing by a human females said absorbent article comprising:
a primary absorbent component having a base, an apex said base and apex each having a width wherein the width of said base is greater than the width of said apex and the width of said primary absorbent component decreases from said base to said apex and at least a portion of said primary absorbent component has a width of less than or equal to about 9.5 mm, said primary absorbent component comprising:
an acquisition/fit portion comprising a hydrophilic flexible, nonionic poltmeric foam structure of interconnected open cells which is capable of absorbing blood and blood-based liquids, said acquisition/fit portion having a first cell size and a first width;
a storage portion als o comprising a hydrophilic, flexible, nonionic polymeric foam structure of interconnected open cells which is capable of absorbing blood and blood-based liquids, having a second cell size and a second width, wherein said second cell size is smaller than said first cell size, creating a capillary gradient, first width is less than said second width, and said acquisition/fit is facing the body of the wearer, wherein said acquisition/fit portion has a resistance to compression deflection of from about 40% to about 85% when measured under a confining pressure of 0.74 psi at 31 degrees C. after 15 minutes, according to the Resistance to Compression Deflection Test, and said storage portions has a resistance to compression deflection of about 5% to about 50% under such conditions.

16. The absorbent article of claim 15 wherein said acquisition/fit portion and said storage portion comprise separate components.

17. The absorbent article of claim 15 wherein said acquisition/fit portion is more compressible and resilient than said storage portion.

18. The absorbent article of claim 15 wherein at least said acquisition/fit portion is able to fit in the space between the wearer's labia.

19. The absorbent article of claim 16 wherein said acquisition/fit component has a capillary suction specific surface area of from about 0.012 to about 0.020 $m^2/cc$ and said storage component has a capillary specific surface area higher than that of said acquisition fit component and in the range of from about 0.020 to about 0.026 $m^2/cc$.

20. A compound sanitary napkin comprising a primary absorbent component and a secondary absorbent component;
said primary absorbent core and an outer cover, said absorbent core comprising a compressible, hydrophilic, flexible, nonionic polymeric foam structure of interconnected open cells which is capable of absorbing blood and blood-based liquids, said foam structure comprising:

an acquisition/fit portion having a resistance to compression deflection, according to the Resistance to Compression Deflection Test, of from about 40% to about 85% when measured under a confining pressure of 0.74 psi at 31 degrees C. after 15 minutes, a capillary specific surface area, according to the Capillary Suction Specific Surface Area Test, of from about 012 to about 0.020 m$^2$/cc, and an average cell diameter of between about 100–130 microns; and a storage portion having a resistance to compression deflection of from about 5% to about 50% under the same conditions specified for said acquisition/fit portion, a capillary specific surface area of from about 0.020 to about 0.026 m$^2$/cc, and an average cell diameter of between about 35–60 microns; and said secondary absorbent component comprising a liquid pervious topsheet, a liquid impervious backsheet joined to said topsheet, and an absorbent element positioned between said topsheet and said backsheet, said secondary absorbent component being joined to said primary absorbent component.

21. The absorbent article of claim 20 wherein said primary absorbent member has a capacity and said secondary absorbent member has a capacity, and the ratio of the capacity of the primary absorbent member to the capacity of said secondary absorbent member is between about 1:1 and about 10:1.

22. The absorbent article of claim 20 wherein said primary absorbent member has a capacity and said secondary absorbent member has a capacity, and the ratio of the capacity of the primary absorbent member to the capacity of said secondary absorbent member is about 5:1.

* * * * *

UNITED STATES PATENT AND TRADEMARK OFFICE
CERTIFICATE OF CORRECTION

PATENT NO. : 5,873,869  
DATED : February 23, 1999  
INVENTOR(S) : John L. Hammons et al.

Page 1 of 1

It is certified that error appears in the above-identified patent and that said Letters Patent is hereby corrected as shown below:

Column 6,  
Line 64, "ateral" should read -- lateral --.

Column 40,  
Line 13, "females" should read -- female --.  
Line 24, "poltmeric" should read -- polymeric --.  
Line 28, "als o" should read -- also --.  
Line 41, "portions" should read -- portion --.

Column 41,  
Line 8, "012" should read -- 0.012 --.

Signed and Sealed this

Sixteenth Day of April, 2002

Attest:

JAMES E. ROGAN  
*Director of the United States Patent and Trademark Office*

*Attesting Officer*